US011801256B2

(12) United States Patent
Liechti et al.

(10) Patent No.: US 11,801,256 B2
(45) Date of Patent: Oct. 31, 2023

(54) ANTIDEPRESSANT-PSILOCYBIN CO-TREATMENT TO ASSIST PSYCHOTHERAPY

(71) Applicant: Universitätsspital Basel, Basel (CH)

(72) Inventors: Matthias Emanuel Liechti, Oberwil (CH); Anna Margarete Becker, Suhr (CH)

(73) Assignee: Universitätsspital Basel, Basel (CH)

( * ) Notice: Subject to any disclaimer, the term of this patent is extended or adjusted under 35 U.S.C. 154(b) by 0 days.

(21) Appl. No.: 17/692,105

(22) Filed: Mar. 10, 2022

(65) Prior Publication Data

US 2022/0387456 A1    Dec. 8, 2022

Related U.S. Application Data

(60) Provisional application No. 63/208,130, filed on Jun. 8, 2021.

(51) Int. Cl.
| | | |
|---|---|---|
| *A61K 31/675* | (2006.01) | |
| *A61P 25/22* | (2006.01) | |
| *A61P 25/24* | (2006.01) | |
| *A61K 31/343* | (2006.01) | |

(52) U.S. Cl.
CPC .......... *A61K 31/675* (2013.01); *A61K 31/343* (2013.01); *A61P 25/22* (2018.01); *A61P 25/24* (2018.01)

(58) Field of Classification Search
CPC .................................................. A61K 31/675
See application file for complete search history.

(56) References Cited

U.S. PATENT DOCUMENTS

2022/0096504 A1†  3/2022  Blumstock

FOREIGN PATENT DOCUMENTS

WO    2021030571    †  2/2021

OTHER PUBLICATIONS

Becker, Clinical Pharmacology & Therapeutics, 111,(4), 886-895.*
Busby, The Intercept, Jul. 28, 2023.*
Akimoto H, Oshima S, Sugiyama T, Negishi A, Nemoto T, & Kobayashi D (2019). Changes in brain metabolites related to stress resilience: metabolomic analysis of the hippocampus in a rat model of depression. Behav Brain Res 359: 342-352.
Andersson M, Persson M, & Kjellgren A (2017). Psychoactive substances as a last resort-a qualitative study of self-treatment of migraine and cluster headaches. Harm Reduct J 14: 60.
Barrett FS, Johnson MW, & Griffiths RR (2015). Validation of the revised Mystical Experience Questionnaire in experimental sessions with psilocybin. J Psychopharmacol 29: 1182-1190.
Becker AM, Holze F, Grandinetti T, Klaiber A, Toedtli VE, Kolaczynska KE, Duthaler U, Varghese N, Eckert A, Grunblatt E, & Liechti ME (2021). Acute effects of psilocybin after escitalopram or placebo pretreatment in a randomized, double-blind, placebo-controlled, cross-over study in healthy subjects. Clin Pharmacol Ther: doi: 10.1002/cpt.2487.
Black K, Shea C, Dursun S, & Kutcher S (2000). Selective serotonin reuptake inhibitor discontinuation syndrome: proposed diagnostic criteria. J Psychiatry Neurosci 25: 255-261.
Bogenschutz MP (2013). Studying the effects of classic hallucinogens in the treatment of alcoholism: rationale, methodology, and current research with psilocybin. Curr Drug Abuse Rev 6: 17-29.
Bogenschutz MP, Forcehimes AA, Pommy JA, Wilcox CE, Barbosa PC, & Strassman RJ (2015). Psilocybin-assisted treatment for alcohol dependence: a proof-of-concept study. J Psychopharmacol 29: 289-299.
Bonson KR, Buckholtz JW, & Murphy DL (1996). Chronic administration of serotnergic antidepressants attenuates the subjective effects of LSD in humans. . Neuropsychopharmacology 14: 425-436.
Bonson KR, & Murphy DL (1996). Alterations in response to LSD in humans associated with chronic administration of tricyclic antidepressants, monoamine oxidase inhibitors or lithium. Behav Brain Res 73: 229-233.
Carhart-Harris R, Giribaldi B, Watts R, Baker-Jones M, Murphy-Beiner A, Murphy R, Martell J, Blemings A, Erritzoe D, & Nutt DJ (2021). Trial of psilocybin versus escitalopram for depression. N Engl J Med 384: 1402-1411.
Carhart-Harris RL, Bolstridge M, Day CMJ, Rucker J, Watts R, Erritzoe DE, Kaelen M, Giribaldi B, Bloomfield M, Pilling S, Rickard JA, Forbes B, Feilding A, Taylor D, Curran HV, & Nutt DJ (2018). Psilocybin with psychological support for treatment-resistant depression: six-month follow-up. Psychopharmacology (Berl) 235: 399-408.
Carhart-Harris RL, Bolstridge M, Rucker J, Day CM, Erritzoe D, Kaelen M, Bloomfield M, Rickard JA, Forbes B, Feilding A, Taylor D, Pilling S, Curran VH, & Nutt DJ (2016). Psilocybin with psychological support for treatment-resistant depression: an open-label feasibility study. Lancet Psychiatry 3: 619-627.
Carhart-Harris RL, & Goodwin GM (2017). The therapeutic potential of psychedelic drugs: past, present, and future. Neuropsychopharmacology 42: 2105-2113.
Davis AK, Barrett FS, May DG, Cosimano MP, Sepeda ND, Johnson MW, Finan PH, & Griffiths RR (2021). Effects of psilocybin-assisted therapy on major depressive disorder: a randomized clinical trial. JAMA Psychiatry 78: 481-489.

(Continued)

*Primary Examiner* — Nizal S Chandrakumar
(74) *Attorney, Agent, or Firm* — Kohn and Associates PLLC

(57) ABSTRACT

A method of enhancing positive effects of a psychedelic, by pretreating an individual with an antidepressant, administering a psychedelic to the individual, and inducing a more positive psychological state in the individual with the antidepressant-psychedelic combination compared with the psychedelic alone. A method of enhancing positive effects of a psychedelic, by inhibiting serotonin transport in an individual, increasing levels of endogenous monoamines in the individual, and stimulating 5-HT$_{2A}$ receptors in the individual. A composition including an antidepressant and a psychedelic in the same dosage form.

8 Claims, 33 Drawing Sheets

(56) References Cited

OTHER PUBLICATIONS

De Almeida RN, Galvao ACM, da Silva FS, Silva E, Palhano-Fontes F, Maia-de-Oliveira JP, de Araujo LB, Lobao-Soares B, & Galvao-Coelho NL (2019). Modulation of serum brain-derived neurotrophic factor by a single dose of ayahuasca: observation from a randomized controlled trial. Front Psychol 10: 1234.
De Montigny C, Chaput Y, & Blier P (1990). Modification of serotonergic neuron properties by long-term treatment with serotonin reuptake blockers. J Clin Psychiatry 51 Suppl B: 4-8.
DeMaar EWJ, Williams HL, Miller AI, & Pfeiffer CC (1960). Effects in man of single and combined oral doses of reserpine, iproniazid, and D-lysergic acid diethylamide. Clin Pharmacol Ther 1: 23-30.
Dittrich A (1998). The standardized psychometric assessment of altered states of consciousness (ASCs) in humans. Pharmacopsychiatry 31 (Suppl 2): 80-84.
Dominguez-Clave E, Soler J, Elices M, Pascual JC, Alvarez E, de la Fuente Revenga M, Friedlander P, Feilding A, & Riba J (2016). Ayahuasca: Pharmacology, neuroscience and therapeutic potential. Brain Res Bull 126: 89-101.
Dong C, Ly C, Dunlap LE, Vargas MV, Sun J, Hwang IW, Azinfar A, Oh WC, Wetsel WC, Olson DE, & Tian L (2021). Psychedelic-inspired drug discovery using an engineered biosensor. Cell 184: 2779-2792.e2718.
Dos Santos RG, Osorio FL, Crippa JA, Riba J, Zuardi AW, & Hallak JE (2016). Antidepressive, anxiolytic, and antiaddictive effects of ayahuasca, psilocybin and lysergic acid diethylamide (LSD): a systematic review of clinical trials published in the last 25 years. Ther Adv Psychopharmacol 6: 193-213.
FDA (2017). Lexapro (Escitalopram) drug label (Reference ID: 4036381). In FDA.
Florio V, Porcelli S, Saria A, Serretti A, & Conca A (2017). Escitalopram plasma levels and antidepressant response. Eur Neuropsychopharmacol 27: 940-944.
Garcia-Romeu A, Davis AK, Erowid F, Erowid E, Griffiths RR, & Johnson MW (2019). Cessation and reduction in alcohol consumption and misuse after psychedelic use. J Psychopharmacol: 269881119845793.
Garcia-Romeu A, Griffiths RR, & Johnson MW (2014). Psilocybin-occasioned mystical experiences in the treatment of tobacco addiction. Curr Drug Abuse Rev 7: 157-164.
Gasser P, Holstein D, Michel Y, Doblin R, Yazar-Klosinski B, Passie T, & Brennseisen R (2014). Safety and efficacy of lysergic acid diethylamide-assisted psychotherapy for anxiety associated with life-threatening diseases. J Nerv Ment Dis 202: 513-520.
Gasser P, Kirchner K, & Passie T (2015). LSD-assisted psychotherapy for anxiety associated with a life-threatening disease: a qualitative study of acute and sustained subjective effects. J Psychopharmacol 29: 57-68.
Gillman PK (2010). Triptans, serotonin agonists, and serotonin syndrome (serotonin toxicity): a review. Headache 50: 264-272.
Griffiths R, Richards W, Johnson M, McCann U, & Jesse R (2008). Mystical-type experiences occasioned by psilocybin mediate the attribution of personal meaning and spiritual significance 14 months later. J Psychopharmacol 22: 621-632.
Griffiths RR, Johnson MW, Carducci MA, Umbricht A, Richards WA, Richards BD, Cosimano MP, & Klinedinst MA (2016). Psilocybin produces substantial and sustained decreases in depression and anxiety in patients with life-threatening cancer: a randomized double-blind trial. J Psychopharmacol 30: 1181-1197.
Griffiths RR, Richards WA, McCann U, & Jesse R (2006). Psilocybin can occasion mystical-type experiences having substantial and sustained personal meaning and spiritual significance. Psychopharmacology (Berl) 187: 268-283; discussion 284-292.
Grob CS, Danforth AL, Chopra GS, Hagerty M, McKay CR, Halberstadt AL, & Greer GR (2011). Pilot study of psilocybin treatment for anxiety in patients with advanced-stage cancer. Arch Gen Psychiatry 68: 71-78.
Grof S, & Dytrych Z (1965). Blocking of LSD reaction by premedication with Niamid. Act Nerv Super (Praha) 7: 306.
Grunblatt E, Bartl J, Zehetmayer S, Ringel TM, Bauer P, Riederer P, & Jacob CP (2009). Gene expression as peripheral biomarkers for sporadic Alzheimer's disease. J Alzheimers Dis 16: 627-634.
Haile CN, Murrough JW, Iosifescu DV, Chang LC, AI Jurdi RK, Foulkes A, Iqbal S, Mahoney JJ, 3rd, De La Garza R, 2nd, Charney DS, Newton TF, & Mathew SJ (2014). Plasma brain derived neurotrophic factor (BDNF) and response to ketamine in treatment-resistant depression. Int J Neuropsychopharmacol 17: 331-336.
Hasler F, Bourquin D, Brenneisen R, Bar T, & Vollenweider FX (1997). Determination of psilocin and 4-hydroxyindole-3-acetic acid in plasma by HPLC-ECD and pharmacokinetic profiles of oral and intravenous psilocybin in man. Pharm Acta Helv 72: 175-184.
Hintzen A, & Passie T (2010) The pharmacology of LSD: a critical review. Oxford University Press: Oxford.
Holze F, Duthaler U, Vizeli P, Muller F, Borgwardt S, & Liechti ME (2019). Pharmacokinetics and subjective effects of a novel oral LSD formulation in healthy subjects. Br J Clin Pharmacol 85: 1474-1483.
Holze F, Vizeli P, Ley L, Muller F, Dolder P, Stocker M, Duthaler U, Varghese N, Eckert A, Borgwardt S, & Liechti ME (2021). Acute dose-dependent effects of lysergic acid diethylamide in a double-blind placebo-controlled study in healthy subjects. Neuropsychopharmacology 46: 537-544.
Hutten N, Mason NL, Dolder P, Theunissen EL, Holze F, Liechti ME, Varghese N, Eckert A, Feilding A, Ramaekers JG, & Kuypers KP (2020). Low doses of LSD acutely increases BDNF blood plasma levels in healthy volunteers. ACS Pharmacol Transl Sci 4: 461-466.
Hysek CM, Vollenweider FX, & Liechti ME (2010). Effects of a b-blocker on the cardiovascular response to MDMA (ecstasy). Emerg Med J 27: 586-589.
Janke W, & Debus G (1978) Die Eigenschaftswörterliste. Hogrefe: Göttingen.
Johnson MW, Garcia-Romeu A, Cosimano MP, & Griffiths RR (2014). Pilot study of the 5-HT2AR agonist psilocybin in the treatment of tobacco addiction. J Psychopharmacol 28: 983-992.
Johnson MW, Garcia-Romeu A, & Griffiths RR (2016). Long-term follow-up of psilocybin-facilitated smoking cessation. Am J Drug Alcohol Abuse 43: 55-60.
Koenig AM, & Thase ME (2009). First-line pharmacotherapies for depression—what is the best choice? Pol Arch Med Wewn 119: 478-486.
Kolaczynska KE, Liechti ME, & Duthaler U (2021). Development and validation of an LC-MS/MS method for the bioanalysis of psilocybin's main metabolites, psilocin and 4-hydroxyindole-3-acetic acid, in human plasma. J Chromatogr B Analyt Technol Biomed Life Sci 1164: 122486.
Krebs TS, & Johansen PO (2012). Lysergic acid diethylamide (LSD) for alcoholism: meta-analysis of randomized controlled trials. J Psychopharmacol 26: 994-1002.
Liechti ME (2017). Modern clinical research on LSD. Neuropsychopharmacology 42: 2114-2127.
Liechti ME, Dolder PC, & Schmid Y (2017). Alterations in conciousness and mystical-type experiences after acute LSD in humans. Psychopharmacology 234: 1499-1510.
Ly C, Greb AC, Cameron LP, Wong JM, Barragan EV, Wilson PC, Burbach KF, Soltanzadeh Zarandi S, Sood A, Paddy MR, Duim WC, Dennis MY, McAllister AK, Ori-McKenney KM, Gray JA, & Olson DE (2018). Psychedelics promote structural and functional neural plasticity. Cell Rep 23: 3170-3182.
Madsen MK, Fisher PM, Burmester D, Dyssegaard A, Stenbaek DS, Kristiansen S, Johansen SS, Lehel S, Linnet K, Svarer C, Erritzoe D, Ozenne B, & Knudsen GM (2019). Psychedelic effects of psilocybin correlate with serotonin 2A receptor occupancy and plasma psilocin levels. Neuropsychopharmacology 44: 1328-1334.
Maracek P, Bakalar E, & Zeman K (1968). Attempt of blocking LSD intoxication with tranylcypromine. Act Nerv 10: 276-277.
Nichols DE (2016). Psychedelics. Pharmacol Rev 68: 264-355.
Nichols DE, Johnson MW, & Nichols CD (2017). Psychedelics as medicines: an emerging new paradigm. Clin Pharmacol Ther 101: 209-219.

(56) References Cited

OTHER PUBLICATIONS

Palhano-Fontes F, Barreto D, Onias H, Andrade KC, Novaes MM, Pessoa JA, Mota-Rolim SA, Osorio FL, Sanches R, Dos Santos RG, Tofoli LF, de Oliveira Silveira G, Yonamine M, Riba J, Santos FR, Silva-Junior AA, Alchieri JC, Galvao-Coelho NL, Lobao-Soares B, Hallak JEC, Arcoverde E, Maia-de-Oliveira JP, & Araujo DB (2019). Rapid antidepressant effects of the psychedelic ayahuasca in treatment-resistant depression: a randomized placebo-controlled trial. Psychol Med 49: 655-663.
Passie T, & Halpern JH (2014). The pharmacology of hallucinogens. In The ASAM principles of addiction medicine. ed Ries R., K. Wolters Kluver: Alphen aan de Rijn, The Netherlands, pp. 235-255.
Passie T, Halpern JH, Stichtenoth DO, Emrich HM, & Hintzen A (2008). The pharmacology of lysergic acid diethylamide: a review. CNS Neurosci Ther 14: 295-314.
Passie T, Seifert J, Schneider U, & Emrich HM (2002). The pharmacology of psilocybin. Addict Biol 7: 357-364.
Pratt Laura A. BDJ, Gu Qiuping (2017). Antidepressant Use Among Persons Aged 12 and Over: United States, 2011-2014. In NCHS data brief Hyattsville, MD: National Center for Health Statistics.
Preller KH, Herdener M, Pokorny T, Planzer A, Kraehenmann R, Stämpfli P, Liechti ME, Seifritz E, & Vollenweider FX (2017). The fabric of meaning and subjective effects in LSD-induced states depend on serotonin 2A receptor activation Curr Biol 27: 451-457.
Rickli A, Moning OD, Hoener MC, & Liechti ME (2016). Receptor interaction profiles of novel psychoactive tryptamines compared with classic hallucinogens. Eur Neuropsychopharmacol 26: 1327-1337.
Roseman L, Nutt DJ, & Carhart-Harris RL (2017). Quality of acute psychedelic experience predicts therapeutic efficacy of psilocybin for treatment-resistant depression. Front Pharmacol 8: 974.
Ross S, Bossis A, Guss J, Agin-Liebes G, Malone T, Cohen B, Mennenga SE, Belser A, Kalliontzi K, Babb J, Su Z, Corby P, & Schmidt BL (2016). Rapid and sustained symptom reduction following psilocybin treatment for anxiety and depression in patients with life-threatening cancer: a randomized controlled trial. J Psychopharmacol 30: 1165-1180.
Rucker JJH, Iliff J, & Nutt DJ (2018). Psychiatry & the psychedelic drugs. Past, present & future. Neuropharmacology 142: 200-218.
Sanches RF, de Lima Osorio F, Dos Santos RG, Macedo LR, Maia-de-Oliveira JP, Wichert-Ana L, de Araujo DB, Riba J, Crippa JA, & Hallak JE (2016). Antidepressant Effects of a Single Dose of Ayahuasca in Patients With Recurrent Depression: A SPECT Study. J Clin Psychopharmacol 36: 77-81.
Schmid Y, Gasser P, Oehen P, & Liechti ME (2021). Acute subjective effects in LSD- and MDMA-assisted psychotherapy. J Psychopharmacol 35: 362-374.
Schmid Y, & Liechti ME (2018). Long-lasting subjective effects of LSD in normal subjects. Psychopharmacology (Berl) 235: 535-545.
Strassman RJ (1992). Human halluciongen interactions with drugs affecting serotonergic neurotransmission. . Neuropsychopharmacology 7: 241-243.
Studerus E, Gamma A, & Vollenweider FX (2010). Psychometric evaluation of the altered states of consciousness rating scale (OAV). PLoS One 5: e12412.
Swissmedic (2020). Arzneimittelinformation Schweizerisches Heilmittelinstitut: Bern.
Tamam L, & Ozpoyraz N (2002). Selective serotonin reuptake inhibitor discontinuation syndrome: a review. Adv Ther 19: 17-26.

Vollenweider FX, & Preller KH (2020). Psychedelic drugs: neurobiology and potential for treatment of psychiatric disorders. Nat Rev Neurosci 21: 611-624.
Vollenweider FX, Vollenweider-Scherpenhuyzen MF, Babler A, Vogel H, & Hell D (1998). Psilocybin induces schizophrenia-like psychosis in humans via a serotonin-2 agonist action. Neuroreport 9: 3897-3902.
Wittchen HU, Wunderlich U, Gruschwitz S, & Zaudig M (1997) SKID-I: Strukturiertes Klinisches Interview für DSM-IV. Hogrefe-Verlag: Göttingen.
Yang T, Nie Z, Shu H, Kuang Y, Chen X, Cheng J, Yu S, & Liu H (2020). The role of BDNF on neural plasticity in depression. Front Cell Neurosci 14: 82-82.
Zerssen DV (1976) Die Beschwerden-Liste. Münchener Informationssystem. Psychis: München.
Gasser et al, Safety and Efficacy of Lysergic Acid Diethylamide-Assisted Psychotherapy for Anxiety Associated With Life-threatening Diseases, pp. 513-520, 2014, Lippincott Williams & Wilkins, Journal of Nervous and Mental Disease.†
Bonson et al, Chronic administration of serotonergic antidepressants attenuates the subjective effects of LSD in human, pp. 425-436, 1996, Springer International Publishing, Neuropsychopharmacology.†
Carhart-Harris et al, Trial of Psilocybin versus Escitalopram for Depression, pp. 1402-1411, 2021, Massachusetts Medical Society, The New England Journal of Medicine.†
Carhart-Harris et al, Psilocybin with psychological support for treatment-resistant depression: six-month follow-up, pp. 399-408, 2018, Springer, Psychopharmacology.†
Sam, A Lysergic-Mescalito Experience LSD & Mescaline, Oct. 13, 2019, Erowid.†
Psychedelic Dreamer, Intense Sadness and Analyzing My Personality DOI & Various, Jul. 25, 2006, Erowid.†
Zoloftshroomer, Interferes with Hallucinations Sertraline (Zoloft) & Various, Jun. 6, 2008, Erowid.†
Windup Godzilla, Grand Reception at Tron Valhalla Mushroom, Jan. 29, 2019, Erowid.†
The Ovoid Kid, Lexapro and Its Effect on Tryptamines Escitalopram, Psilocybin, LSD & DMT, Jan. 31, 2021, Erowid.†
Bonson et al, Alterations in responses to Lsd in humans associated with chronic administration of tricyclic antidepressants, monoamine oxidase inhibitors or lithium, pp. 229-233, 1996, Elsevier, Behavioural Brain Research.†
Jha et al, When Discontinuing SSRI Antidepressants Is a Challenge: Management Tips, pp. 1176-1184, 2018, American Psychiatric Association, The American Journal of Psychiatry.†
LatentSanityDisorder, Remeron-berance of Things Past Mirtazapine & Various, Jan. 11, 2013, Erowid.†
Baker, Getting on the Train with Dimitri DMT, Apr. 16, 2008, Erowid.†
Madsen et al, Psychedelic effects of psilocybin correlate with serotonin 2A receptor occupancy and plasma psilocin levels, p. 1328-1334, 2019, Springer International Publishing, Neuropsychopharmacology.†
Chung et al, Pharmacokinetics and effect on the corrected QT interval of single-dose escitalopram in healthy elderly compared with younger adults, pp. 20-26, 2017, Wolters Kluwer Health, Inc, International Clinical Psychopharmacology.†
Tsujikawa et al, Morphological and chemical analysis of magic mushrooms in Japan, p. 85-90, 2003, Elsevier, Forensic Science International.†

\* cited by examiner
† cited by third party

Psilocybin

Escitalopram

FIG. 24

Mean values and statistics for the acute subjective effects of psilocybin after escitalopram or placebo

|  |  | Escitalopram (mean ± SEM) | Placebo mean ± SEM | t(22) | p |
|---|---|---|---|---|---|
| Any drug effect | $\Delta E_{max}$ | 73 ± 7 | 85 ± 6 | 2.6 | 0.015 * |
| Good drug effect | $\Delta E_{max}$ | 76 ± 6 | 79 ± 6 | 0.6 | 0.571 |
| Bad drug effect | $\Delta E_{max}$ | 18 ± 5 | 39 ± 7 | 3.3 | 0.004 ** |
| Drug liking | $\Delta E_{max}$ | 75 ± 7 | 78 ± 7 | 0.5 | 0.616 |
| High | $\Delta E_{max}$ | 73 ± 7 | 75 ± 7 | 0.2 | 0.875 |
| Stimulated | $\Delta E_{max}$ | 68 ± 7 | 75 ± 7 | 1.3 | 0.201 |
| Fear | $\Delta E_{max}$ | 10 ± 4 | 20 ± 6 | 3.2 | 0.004 ** |
| Ego dissolution | $\Delta E_{max}$ | 51 ± 8 | 64 ± 8 | 1.6 | 0.130 |
| Happy | $\Delta E_{max}$ | 30 ± 4 | 30 ± 4 | 0.1 | 0.905 |
|  | $\Delta E_{min}$ | -3 ± 2 | -11 ± 4 | -2.2 | 0.041 * |
| Trust | $\Delta E_{max}$ | 25 ± 5 | 28 ± 4 | 0.9 | 0.404 |
|  | $\Delta E_{min}$ | -2 ± 2 | -7 ± 4 | -1.8 | 0.086 |
| Feeling close to others | $\Delta E_{max}$ | 11 ± 4 | 16 ± 4 | 1.0 | 0.341 |
|  | $\Delta E_{min}$ | -14 ± 4 | -16 ± 4 | -0.2 | 0.833 |
| Talkative | $\Delta E_{max}$ | 9 ± 3 | 17 ± 3 | 2.3 | 0.029 * |
|  | $\Delta E_{min}$ | -28 ± 4 | -28 ± 4 | 0.0 | 0.978 |
| Open | $\Delta E_{max}$ | 18 ± 4 | 24 ± 4 | 2.4 | 0.027 * |
|  | $\Delta E_{min}$ | -16 ± 4 | -17 ± 4 | -0.1 | 0.947 |
| Speed of thinking | $\Delta E_{max}$ | 11 ± 4 | 14 ± 3 | 1.0 | 0.332 |
|  | $\Delta E_{min}$ | -28 ± 4 | -30 ± 4 | -0.6 | 0.534 |
| Perception of time | $\Delta E_{max}$ | 9 ± 3 | 16 ± 4 | 1.7 | 0.110 |
|  | $\Delta E_{min}$ | -28 ± 3 | -28 ± 4 | 0.2 | 0.826 |
| Concentration | $\Delta E_{max}$ | 12 ± 3 | 15 ± 4 | 1.1 | 0.278 |
|  | $\Delta E_{min}$ | -27 ± 4 | -35 ± 3 | -2.7 | 0.012 * |

*p < 0.05, p < 0.01, *p < 0.001; $\Delta E_{max}$, maximal difference from baseline; $\Delta E_{min}$, minimal difference from baseline

FIG. 25

Mean values and statistics for the acute subjective effects of psilocybin after escitalopram and placebo

|  |  | Escitalopram (mean ± SEM) | Placebo (mean ± SEM) | t(22) | p |
|---|---|---|---|---|---|
| Adjective Mood Rating Scale (AMRS score) | | | | | |
| Concentration | $\Delta E_{max}$ | -0.4 ± 0.6 | 0.3 ± 0.4 | 1.3 | 0.203 |
| Activity | $\Delta E_{max}$ | 1.4 ± 0.4 | 0.6 ± 0.6 | -1.2 | 0.252 |
| Extroverion | $\Delta E_{max}$ | 0.9 ± 0.5 | 1.4 ± 0.6 | 0.8 | 0.411 |
| Introversion | $\Delta E_{max}$ | 3.7 ± 0.7 | 3.6 ± 0.5 | -0.2 | 0.817 |
| General well-being | $\Delta E_{max}$ | 3.7 ± 0.9 | 3.7 ± 1.1 | 0.0 | 1.000 |
| Excitability | $\Delta E_{max}$ | 0.2 ± 0.3 | 1.1 ± 0.5 | 2.3 | 0.031 * |
| Sensitivity | $\Delta E_{max}$ | 2.2 ± 0.4 | 3.2 ± 0.5 | 2.2 | 0.035 * |
| Anxiety | $\Delta E_{max}$ | 0.3 ± 0.2 | 1.5 ± 0.3 | 3.0 | 0.007 ** |

*p < 0.05, p < 0.01, *p < 0.001; $\Delta E_{max}$, maximal difference from baseline

FIG. 26

Acute mind-altering effects of psilocybin after escitalopram and placebo

|  |  | Escitalopram (mean ± SEM) | Placebo (mean ± SEM) | t (22) | p |
|---|---|---|---|---|---|
| 5 Dimensions of Altered States of Consciousness (ASC) Scale | | | | | |
| Oceanic boundlessness | % score | 39 ± 5 | 39 ± 6 | 0.0 | 0.974 |
| Anxious ego-dissolution | % score | 15 ± 3 | 25 ± 4 | 2.3 | 0.029 * |
| Visionary restructuralization | % score | 41 ± 6 | 43 ± 5 | 0.2 | 0.864 |
| OAV total score | % score | 32 ± 4 | 35 ± 4 | 0.8 | 0.412 |
| Auditory alterations | % score | 12 ± 4 | 12 ± 4 | 0.0 | 0.985 |
| Reductions of vigilance | % score | 40 ± 5 | 44 ± 4 | 0.7 | 0.474 |
| ASC total score | % score | 29 ± 4 | 32 ± 4 | 0.8 | 0.450 |
| Experience of unity | % score | 36 ± 6 | 38 ± 7 | 0.4 | 0.659 |
| Spiritual experience | % score | 24 ± 5 | 26 ± 7 | 0.4 | 0.716 |
| Blissful state | % score | 43 ± 6 | 44 ± 8 | 0.1 | 0.909 |
| Insightfulness | % score | 34 ± 6 | 37 ± 7 | 0.4 | 0.661 |
| Disembodiment | % score | 37 ± 7 | 34 ± 7 | -0.4 | 0.711 |
| Impaired control and cognition | % score | 27 ± 5 | 34 ± 5 | 1.6 | 0.125 |
| Anxiety | % score | 7 ± 3 | 20 ± 5 | 2.4 | 0.026 * |
| Complex imagery | % score | 46 ± 8 | 44 ± 8 | -0.2 | 0.861 |
| Elementary imagery | % score | 51 ± 8 | 59 ± 7 | 1.3 | 0.224 |
| Audio-visual synesthesia | % score | 46 ± 8 | 44 ± 9 | -0.3 | 0.738 |
| Changed meaning of percepts | % score | 31 ± 5 | 27 ± 5 | -0.7 | 0.502 |

Acute mystical experiences induced by psilocybin after escitalopram and placebo

|  |  | Escitalopram (mean ± SEM) | Placebo (mean ± SEM) | t (22) | p |
|---|---|---|---|---|---|
| Mystical Experience Questionnaire (MEQ43) |  |  |  |  |  |
| Internal unity | % score | 29 ± 5 | 28 ± 6 | -0.1 | 0.958 |
| External unity | % score | 28 ± 5 | 32 ± 6 | 0.7 | 0.471 |
| Sacredness | % score | 31 ± 5 | 31 ± 6 | 0.1 | 0.931 |
| Noetic quality | % score | 27 ± 5 | 32 ± 5 | 1.0 | 0.349 |
| Deeply felt positive mood | % score | 46 ± 6 | 42 ± 7 | -0.6 | 0.537 |
| Transcendence of time/space | % score | 38 ± 5 | 44 ± 5 | 1.2 | 0.240 |
| Ineffability | % score | 35 ± 4 | 42 ± 5 | 1.7 | 0.113 |
| Nadir | % score | 9 ± 2 | 22 ± 4 | 3.7 | 0.001 ** |
| Aesthetic Experience | % score | 42 ± 6 | 40 ± 5 | -0.4 | 0.706 |
| Mystical Experience Questionnaire (MEQ30) |  |  |  |  |  |
| Mystical | % score | 28 ± 5 | 30 ± 6 | 0.4 | 0.718 |
| Positive mood | % score | 47 ± 5 | 44 ± 6 | -0.4 | 0.701 |
| Transcendence of time/space | % score | 38 ± 5 | 46 ± 6 | 1.5 | 0.157 |
| Ineffability | % score | 46 ± 5 | 57 ± 5 | 2.6 | 0.017 * |
| MEQ30 total score | % score | 36 ± 4 | 39 ± 5 | 0.7 | 0.471 |

Mean values and statistics for the acute autonimic and adverse effects of psilocybin after escitalopram and placebo.

|  |  | Escitalopram (mean ± SEM) | Placebo (mean ± SEM) | t (22) | p |  |
|---|---|---|---|---|---|---|
| Systolic blood pressure (mmHg) | $\Delta E_{max}$ | 9 ± 1 | 16 ± 2 | 4.4 | 0.000 | *** |
| Diastolic blood pressure (mmHg) | $\Delta E_{max}$ | 13 ± 1 | 17 ± 1 | 2.6 | 0.017 | * |
| Heart rate (beats/min) | $\Delta E_{max}$ | 6 ± 1 | 9 ± 1 | 1.8 | 0.087 |  |
| Rate pressure product | $\Delta E_{max}$ | 840 ± 139 | 1808 ± 200 | 3.8 | 0.001 | ** |
| Mean arterial pressure | $\Delta E_{max}$ | 10 ± 1 | 16 ± 1 | 3.6 | 0.002 | ** |
| Body temperature (°C) | $\Delta E_{max}$ | 0.8 ± 0.1 | 0.9 ± 0.1 | 0.9 | 0.355 |  |
| QTc interval (ms) | -1h | 404 ± 5 | 398 ± 4 | 1.3 | 0.214 |  |
|  | 2.5h | 397 ± 8 | 388 ± 7 | 1.5 | 0.157 |  |
|  | $\Delta E_{-1-2.5h}$ | -7 ± 8 | -10 ± 5 | 0.3 | 0.735 |  |
| Pupil dilation (mm) | $E_{max}$ | 6.7 ± 0.2 | 7.0 ± 0.2 | 3.6 | 0.002 | ** |
|  | $E_{min}$ | 5.1 ± 0.2 | 5.5 ± 0.2 | 5.7 | 0.000 | *** |
|  | $\Delta E_{max}$ | 0.4 ± 0.1 | 1.2 ± 0.1 | 6.2 | 0.000 | *** |
|  | $\Delta E_{min}$ | 0.5 ± 0.1 | 1.5 ± 0.1 | 8.5 | 0.000 | *** |
| Pupil contraction (mm) | $\Delta E_{min}$ | -0.2 ± 0.0 | -0.4 ± 0.1 | -3.6 | 0.002 | ** |
| List of Complaints (LC score) |  |  |  |  |  |  |
| Complaints at baseline | -1h | 2 ± 1 | 1 ± 1 | -1.2 | 0.257 |  |
| Acute adverse effects | 0-7h | 9 ± 2 | 12 ± 2 | 2.4 | 0.028 | * |
| Adverse effects | $\Delta E_{0-7h}$ | 7 ± 2 | 10 ± 2 | 2.7 | 0.012 | * |

*p < 0.05, p < 0.01, *p < 0.001; $E_{max}$, maximal effect; $\Delta E_{max}$, maximal difference from baseline; $\Delta E_{min}$, minimal difference from baseline

FIG. 29

Pharmacokinetic parameters [mean±SD, range]

| | $C_{max}$ (ng/mL) | $t_{max}$ (h) | $t_{1/2}$ (h) | $AUC_7$ (ng·h/mL) | $AUC_\infty$ (ng·h/mL) |
|---|---|---|---|---|---|
| Escitalopram | | | | | |
| Psilocin unconj. | 22±8.5 | 2 | 2.0±0.5 | 72±18 | 84±21 |
| | 12-50 | 1-3 | 1.5-3.7 | 46-110 | 55-127 |
| Psilocin glucuronide | 82±30 | 4 | 5.7±2.4 | 364±116 | 822±364 |
| | 46-183 | 2.5-6 | 2.8-10.7 | 204-727 | 370-1819 |
| Psilocin total | 97±33 | 3 | 4.8±1.8 | 436±119 | 851±322 |
| | 53-207 | 2-5 | 2.7-8.8 | 252-813 | 442-1691 |
| 4-HIAA | 106±37 | 2 | 1.7±0.5 | 328±80 | 367±84 |
| | 57-199 | 0.75-3 | 1.3-3.6 | 214-458 | 231-523 |
| Escitalopram | 44±20 | 2.75 | | | |
| | 25-116 | 1.9-7 | | | |
| Placebo | | | | | |
| Psilocin unconj. | 20±5.4 | 2 | 1.8±0.3 | 73±17 | 83±21 |
| | 11-36 | 1-4 | 1.1-2.2 | 46-102 | 50-118 |
| Psilocin glucuronide | 82±28 | 4 | 4.7±1.6 | 373±126 | 712±243 |
| | 40-165 | 3-7 | 2.5-8.2 | 203-728 | 343-1262 |
| Psilocin total | 96±28 | 3 | 4.3±1.3 | 446±124 | 798±259 |
| | 50-181 | 2-7 | 2.4-6.8 | 280-802 | 414-1382 |
| 4-HIAA | 105±30 | 2 | 1.6±0.3 | 317±66 | 347±72 |
| | 52-154 | 0.5-4 | 1.0-2.3 | 205-409 | 226-447 |

AUC, area under the plasma concentration-time curve; $AUC_\infty$, AUC from time zero to infinity; $AUC_7$, from time 0-7 h; $C_{max}$, maximum observed plasma concentration; total, after deglucuronidation (unconjugated + glucuronide); unconj., unconjugated; $T_{1/2}$, plasma half-life; $T_{max}$, time to reach $C_{max}$; 4-HIAA, 4-hydroxyindole-3-acetic acid. Data are mean±SD except for $t_{max}$ (median and range)

Effects of escitalopram and placebo on BDNF plasma concentrations after

| Time | Escitalopram BDNF (pg/ml) mean ± SEM | Placebo BDNF (pg/ml) mean ± SEM | t(22) | p |
|---|---|---|---|---|
| 0h | 3064.52 ± 539.35 | 2929.81 ± 477.33 | 0.27863 | 0.7831 |
| 4h | 3169.19 ± 426.47 | 4282.5 ± 785.45 | -1.4841 | 0.152 |
| 7h | 3928.06 ± 511.94 | 3808.43 ± 643.94 | 0.22788 | 0.8218 |
| Δ4h | 104.67 ± 421.7 | 1352.68 ± 672.63 | -1.4921 | 0.1499 |
| Δ7h | 863.54 ± 432.33 | 878.62 ± 550.92 | -0.022035 | 0.9826 |
| Emax | 4743.83 ± 521.36 | 5078.01 ± 734.79 | -0.5613 | 0.5803 |
| ΔEmax | 1679.31 ± 311.35 | 2148.19 ± 604.33 | -0.81156 | 0.4257 |

ANTIDEPRESSANT-PSILOCYBIN CO-TREATMENT TO ASSIST PSYCHOTHERAPY

BACKGROUND OF THE INVENTION

1. Technical Field

The present invention relates to the use of an antidepressant together with psilocybin, psilocybin analogs or derivatives, related psychedelics or psychoplastogens to induce a psychedelic state and assisting psychotherapy and treating medical conditions.

2. Background Art

Hallucinogens or psychedelics are substances capable of inducing exceptional subjective effects such as a dream-like alteration of consciousness, pronounced affective changes, enhanced introspective abilities, visual imagery, pseudo-hallucinations, synesthesia, mystical-type experiences, and experiences of ego dissolution (Holze et al., 2021; Liechti, 2017; Passie et al., 2008).

Psychedelics have also newly been termed psychoplastogens because these substances also exhibit neuroregenerative effects that can contribute to their therapeutic effects (Ly et al., 2018). Neuroplastogenic effects can be present to various extents in a given psychedelic or derivative thereof (Dong et al., 2021). Neuroregenerative effects can also be present in the absence of subjective psychedelic effects in a given compound or at a dose of a compound that is without psychedelic effects (Dong et al., 2021).

Efficacy of psychedelics for the treatment of medical conditions has been shown in clinical trials using psilocybin in patients with major depression (Carhart-Harris et al., 2016; Davis et al., 2021; Griffiths et al., 2016; Roseman et al., 2017; Ross et al., 2016), anxiety disorder or anxiety associated with terminal illness (Griffiths et al., 2016; Grob et al., 2011; Ross et al., 2016), and in different forms of addiction (Bogenschutz, 2013; Bogenschutz et al., 2015; Garcia-Romeu et al., 2019; Garcia-Romeu et al., 2014; Johnson et al., 2014; Johnson et al., 2016) and using lysergic acid diethylamide (LSD) in patients with addiction (Krebs & Johansen, 2012), in patients with anxiety associated with life-threatening illness (Gasser et al., 2014; Gasser et al., 2015). There is also evidence that the psychedelic brew Ayahuasca, which contains the active psychedelic substance N,N-dimethyltryptamine (DMT) (Dominguez-Clave et al., 2016) can alleviate depression (Dos Santos et al., 2016; Palhano-Fontes et al., 2019; Sanches et al., 2016).

Psychedelics such as psilocybin and LSD can be used to assist psychotherapy for many indications including anxiety, depression, addiction, personality disorder, and others, and can also be used to treat other medical disorders such as cluster headache and migraine and others. Although no psychedelic is currently licensed for medical use, psilocybin and LSD are used already experimentally within clinical trials and special therapeutic (compassionate use) programs (Andersson et al., 2017; Bogenschutz, 2013; Bogenschutz et al., 2015; Gasser et al., 2015; Griffiths et al., 2016; Grob et al., 2011; Krebs & Johansen, 2012; Ross et al., 2016; Schmid et al., 2021).

Psychedelic substances produce their characteristic acute effects in humans via activation of the serotonin 5-$HT_{2A}$ receptor as specifically shown in clinical studies for psilocybin and LSD (Holze et al., 2021; Preller et al., 2017; Vollenweider et al., 1998). All serotonergic psychedelics including LSD, psilocybin, DMT, and mescaline are agonists at the 5-$HT_{2A}$ receptor (Rickli et al., 2016) and can therefore produce overall largely similar effects.

Positive acute subjective psychedelic experiences after administration of psilocybin are correlated with its long-term therapeutic benefits in patients with depression or addiction (Garcia-Romeu et al., 2014; Griffiths et al., 2016; Roseman et al., 2017). This means that the acute effects of a serotonergic psychedelic in humans can be used to predict, at least in part, the therapeutic outcome in patients. Acute effects that can contribute to positive long-term effects of psychedelics including mescaline are effects that are thought to enhance the therapeutic relationship including increased openness, trust, feelings of connectedness or emulsion with persons, insight in psychological problems and stimulation of neuroregenerative processes as described in detail elsewhere (Vollenweider & Preller, 2020).

Psychedelics are typically investigated and used in patients with psychiatric disorders already treated with antidepressant medications, typically of the class of serotonin transporter inhibitors such as escitalopram. In most if not all studies and clinical situations the patients are currently asked to stop their current antidepressant medication before they are treated with a psychedelic. Instructions vary but typically the antidepressant treatment is stopped or paused 1-3 weeks before the administration of the psychedelic. Researchers and physicians assume that the antidepressant treatment interacts negatively with the response to the psychedelic reducing its acute effects. Others assume increased adverse effects if antidepressants and psychedelics are used together including potentially dangerous interactions such as QT-time prolongation leading to an increased risk of cardiac arrhythmia and death or an increased risk of serotonin syndrome. These fears are based on assumptions and old reports in the literature but not based on valid scientific data. Thus, it is not clear whether the combination of an antidepressant and a psychedelic such as psilocybin is problematic or not. Furthermore, patients can often not stop or pause the antidepressant treatment and there is a risk of withdrawal symptoms and relapse when the established antidepressant treatment is stopped or even slowly tampered. Finally, the recently approved novel treatment of depression with nasal ketamine administration marketed as SPRAVATO® (Janssen Pharmaceuticals, Inc.) which has similarity to psychedelics can only be administered in patients already treated with an antidepressant. Taken together, psychedelics can be effective treatments for psychiatric and other disorders that can, however, require additional antidepressant treatment.

There remains a need for effective antidepressant treatment.

SUMMARY OF THE INVENTION

The present invention provides for a method of enhancing positive effects of a psychedelic, by pretreating an individual with an antidepressant, administering a psychedelic to the individual, and inducing a more positive psychological state in the individual with the antidepressant-psychedelic combination compared with the psychedelic alone.

The present invention also provides for a method of enhancing positive effects of a psychedelic, by inhibiting serotonin transport in an individual, increasing levels of endogenous monoamines in the individual, and stimulating 5-$HT_{2A}$ receptors in the individual.

The present invention also provides for a composition including an antidepressant and a psychedelic in the same dosage form.

DESCRIPTION OF THE DRAWINGS

Other advantages of the present invention are readily appreciated as the same becomes better understood by reference to the following detailed description when considered in connection with the accompanying drawings wherein:

FIG. 24 is a table of the mean values and statistics of the subjective effects of psilocybin on the visual analog scales (VAS) after escitalopram and placebo pretreatment;

FIG. 25 is a table of the mean values and statistics of the subjective effects of psilocybin on the Adjective Mood Rating Scale (AMRS) after escitalopram and placebo pretreatment;

FIG. 26 is a table of the mean values and statistics of the acute mind-altering effects of psilocybin in the 5 Dimensions of Altered States of Consciousness Scale (5D-ASC) after escitalopram and placebo pretreatment;

FIG. 27 is a table of the mean values and statistics of the of the acute effects of psilocybin in the Mystical Experience Questionnaire (MEQ43 and MEQ30) after escitalopram and placebo pretreatment;

FIG. 28 is a table of the mean values and statistics of the acute autonomic and adverse effects of psilocybin after escitalopram and placebo pretreatment;

FIG. 29 is a table of the pharmacokinetic parameters of psilocybin after escitalopram and placebo pretreatment;

DETAILED DESCRIPTION OF THE INVENTION

Figure 1A:
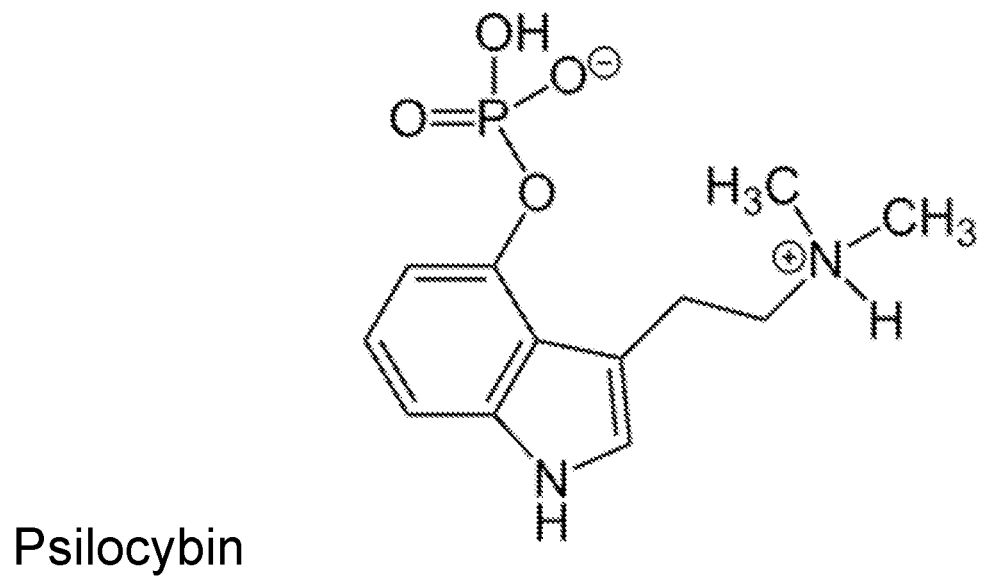
FIG. 1A is a drawing of the chemical structure of psilocybin and FIG. 1B is a drawing of the chemical structure of escitalopram.

The present invention provides for a method of inducing psychedelic states by administering a psychedelic (preferably psilocybin (FIG. 1A)), a salt thereof, analogs thereof, or derivatives thereof in a controlled medical/psychological setting to an individual and inducing a psychedelic state for treating various medical conditions and in an individual co-treated with an antidepressant.

Currently, due to concerns of toxicity and/or ineffectiveness, psychedelics such as psilocybin are administered only in patients not already treated with an antidepressant or in patients where the antidepressant treatment was stopped at least one week before the administration of the psychedelic.

There were reports that the SSRIs fluoxetine or sertraline reduced LSD effects (Bonson et al., 1996; Bonson & Murphy, 1996; Hintzen & Passie, 2010; Strassman, 1992) and it was therefore assumed that antidepressants reduce the response to psychedelics and should be stopped before the use of LSD or psilocybin.

Patients in clinical studies using psilocybin had to be free of concomitant anti-depressants for two weeks prior to randomization and for the duration of the study (Carhart-Harris et al., 2018; Ross et al., 2016) or medications affecting the serotonin system were stopped at least 5 half-lives before psilocybin administration (Griffiths et al., 2016) or study inclusion (Davis et al., 2021) in clinical trials using psilocybin in patients with depression and/or anxiety. This means that current and past research trials performed with psilocybin stopped any antidepressant treatment long before the psilocybin administration. Similarly, patients administered with LSD pause any SSRI treatment typically for 5 days before their LSD treatment sessions (Gasser et al., 2014; Gasser et al., 2015; Schmid et al., 2021).

However, this medical practice of stopping the antidepressant is problematic in many patients needing the antidepressant treatment or suffering from withdrawal when stopping it. Interruption or discontinuation of antidepressants often lead to withdrawal symptoms including mainly dizziness, nausea/vomiting, headache, and lethargy (Black et al., 2000; Tamam & Ozpoyraz, 2002) and can also trigger relapse of depression.

Additionally, there are fears that psychedelics administered jointly with antidepressants would lead to increased adverse effects due to their share serotonergic action and resulting in serotonergic toxicity. Specifically, combinations of SSRIs and serotonin agonists such as triptans, used in the treatment of migraine and which have a very similar structure to the tryptamines including psilocybin, have been associated with increased risk of serotonin syndrome, although this is disputed, and psychedelics such as the ergotamine LSD do not produce serotonin syndrome (Gillman, 2010).

The available evidence and views in the prior art supported the discontinuation of the antidepressant treatment or were unclear. The present invention shows that administering psychedelics with antidepressants can be advantageous.

Figure 1B:
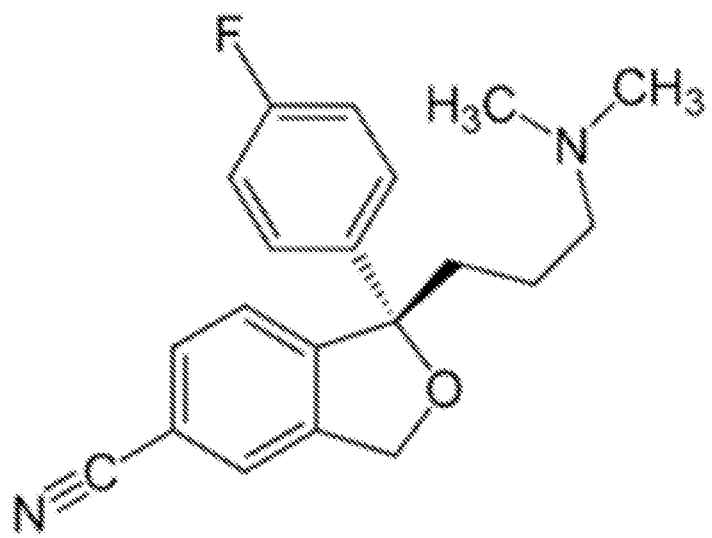

More specifically, the present invention provides for a method of enhancing positive acute and long-term therapeutic effects of a psychedelic, by pretreating an individual with an antidepressant, administering a psychedelic to the individual, and inducing a more positive psychological state in the individual with the antidepressant-psychedelic combination compared with the psychedelic alone. Administering the antidepressant (such as escitalopram (FIG. 1B)) before the psychedelic administration enhances the endogenous serotonin system prior to stimulating the 5-HT$_2$ receptor with the psychedelic and overall induces a positive psychological state in an individual and relatively enhances the positive response to the psychedelic with the antidepressant. The overall goal of the present invention is to improve the positive over negative acute subjective effect response (i.e. improve or maintain good drug effects and reduce bad drug effects) to a psychedelic. The method can be used for any indication of psychedelic medication use and typically applies to indications where a positive experience after psychedelic use predicts the long-term effects such as in psychiatric disorders including (but not limited to) depression, anxiety, anxiety related to life-threatening disease, obsessive-compulsive disorder, personality disorder, and addiction.

"Bad drug effects" as used herein refers to any unwanted effects of the psychedelic, such as, but not limited to subjective bad drug effect, anxiety, fear, anxious-ego dissolution, nadir effects, adverse effects such as rated with a list of complaints and adverse autonomic drug effects such as increases in blood pressure or heart-rate-blood pressure product and combinations thereof.

"Good drug effects" as used herein refers to any desired effects of the psychedelic, such as, but not limited to subjective good drug effects, drug linking, oceanic boundlessness, experience of unity, spiritual experience, blissful state, insightfulness, connectedness, mystical experiences, mystical-type effects, positive mood, transcendence of time/space, ineffability, well-being, trust, feelings of love, feeling open, peak experience, and combinations thereof.

"Treatment outcome" as used herein refers to any change (improvement) in a disorder for which psychedelic-therapy is used and lasting longer than the acute effects of the substances. For example, a good drug effect acutely induced with a psychedelic is known to improve depression in patients with depression and treated with a psychedelic beyond the acute effect of the psychedelic.

The psychedelics used in the methods of the present invention can be, but are not limited to, psilocybin, psilocin, LSD, mescaline, dimethyltryptamine (DMT), 2,5-dimethoxy-4-iodoamphetamine (DOI), 2,5-dimethoxy-4-bromoamphetamie (DOB), other phenethylamine or tryptamine psychedelics, salts thereof, analogs thereof, solvates thereof, isomers thereof, tartrates thereof, prodrugs thereof, deuterated forms thereof, or homologues thereof. While psilocybin is specifically referred to herein, it should be understood that any psychedelic can also be used.

The antidepressant is preferably escitalopram, but can also be generally selected from the classes of selective serotonin reuptake inhibitors (SSRIs) (such as citalopram, fluoxetine, fluvoxamine, paroxetine, or sertraline), serotonin-norepinephrine reuptake inhibitors (SNRIs) (such as desvenlafaxine, duloxetine, levomilnacipran, milnacipran, or venlafaxine), serotonin modulator and stimulators (SMSs) (such as vilazodone or vortioxetine), serotonin antagonist and reuptake inhibitors (SARIs) (such as nefazodone or trazodone), norepinephrine reuptake inhibitors (NRIs) (such as reboxetine, teniloxazine, or viloxazine), norepinephrine-dopamine reuptake inhibitors (NDRIs) (such as bupropion), tricyclic antidepressants (TCAs) (such as amitriptyline, amitriptylinoxide, clomipramine, desipramine, dibenzepin, dimetacrine, dosulepin, doxepin, imipramine, lofepramine, melitracen, nitroxazepine, nortriptyline, noxiptiline, opipramol, pipofezine, protriptyline, or trimipramine), tetracyclic antidepressants (TeCAs) (such as amoxapine, maprotiline, mianserin, mirtazapine, or setiptiline), monoamine oxidase inhibitors (MAOIs) (such as isocarboxazid, phenelzine, tranylcypromine, selegiline, caroxazone, metralindole, moclobemide, pirlindole, toloxatone, or bifemelane), or analogs thereof. The antidepressant can also be a melatonin receptor agonist (such as agomelatine).

Doses commonly used in psilocybin-assisted therapy are 10-30 mg. Doses commonly used in LSD-assisted treatment/psychotherapy are 0.1-0.2 mg. Doses of the psychedelic can be low doses (microdoses) and/or repeatedly administered. Doses of escitalopram are typically 5-20 mg once per day. Doses of the antidepressant are known and reported in the labeling of the manufacturer. The antidepressant can be administered for a duration of time that is short-term (days, weeks, or months) or long-term (months or years) as a pre-treatment or after administering the psychedelic. The psychedelic can be administered short-term or long-term. A first dose of the antidepressant and psychedelic can also be administered at the same time, and subsequently the antidepressant and psychedelic can be administered for the same duration or different durations of time.

The present invention also provides for a composition including an antidepressant and a psychedelic in the same dosage form. The antidepressant and psychedelic can have different or the same release profiles, and either can be included in coatings on a solid dosage unit.

The present invention provides for a method of therapy, by administering a psychedelic to an individual co-treated with an antidepressant and treating the individual.

The present invention includes the description of a clinical study (Becker et al., 2021) comparing the acute effects of a typical dose of psilocybin of 25 mg after escitalopram treatment for 14 days compared with those of psilocybin after placebo treatment using a randomized, double-blind, placebo-controlled cross-over study design in 24 healthy subjects (EXAMPLE 1) which has been published (Becker et al., 2021).

The present invention documents that escitalopram treatment before the administration of a full and typical therapeutic dose of psilocybin improved the acute effects of psilocybin compared to its administration after a placebo treatment. Specifically, escitalopram pretreatment reduced psilocybin-induced bad drug effect, fear, anxiety, anxious ego-dissolution, nadir effects, cardio-stimulant effects, and acute adverse effects compared to psilocybin alone thus resulting in an overall more favorable acute effect profile for psilocybin. See EXAMPLE 1 for a full description.

The induction of an overall positive acute response to the psychedelic is critical because several studies showed that a more positive experience is predictive of a greater therapeutic long-term effect of the psychedelic (Garcia-Romeu et al., 2014; Griffiths et al., 2016; Ross et al., 2016). Even in healthy subjects, positive acute responses to psychedelics have been shown to be linked to more positive long-term effects on well-being (Griffiths et al., 2008; Schmid & Liechti, 2018). A positive overall response similar to representative and therapeutically used doses of psilocybin of 25 mg was documented within the present invention (EXAMPLE 1).

The present invention allows to induce less adverse and negative acute effects and inducing more positive acute effects using a psychedelic and as practically documented using the example of psilocybin after escitalopram pretreatment in EXAMPLE 1.

Psilocybin is a classic serotonergic psychedelic. Pharmacologically, serotonergic psychedelics like psilocybin or LSD are all thought to induce their subjective psychedelic effects primarily via their common stimulation of the $5-HT_{2A}$ receptor. However, there are differences in the receptor activation profiles between the substances that may induce different subjective effects and also differently interact with antidepressants. Psilocin (the active metabolite present in the human body derived from the prodrug psilocybin) stimulates the $5-HT_{2A}$ receptor but additionally inhibits the 5-HT transporter (SERT) similar to the SERT inhibitor escitalopram. LSD potently stimulates the $5-HT_{2A}$ receptor but also $5-HT_{2B/C}$, $5-HT_1$ and $D_{1-3}$ receptors. In contrast to LSD, psilocybin shows no affinity for $D_2$ receptors. Taken together, LSD can have greater dopaminergic activity than psilocybin, and psilocybin can have additional action at the SERT.

Psilocybin in combination with an antidepressant (such as escitalopram daily at doses of 10-20 mg) can be used to assist psychotherapy, typically at acutely psychoactive doses of 10-50 mg, for many indications including anxiety, depression, addiction, personality disorder, and others and can also be used to treat other disorders such as cluster headache, migraine, and others.

Moderate to high doses of psilocybin of 15-30 mg are useful to enhance psychotherapy for most indications including anxiety, depression, compulsive obsessive disorder, eating disorder, post-traumatic stress disorder, addiction (alcohol, nicotine, behavioral, cocaine, amphetamines), anxiety associated with life-threatening illness, adjustment disorder, cluster headache, and migraine.

A high to very high dose of psilocybin (25-50 mg) is particularly useful in cases where a very strong effect is desired. This includes patients were a higher degree of "ego dissolution" is targeted such as patients with cancer, pain, addiction with high tolerance such as opioid dependence and any other disorders such as personality disorder that may need high doses and high ego dissolution effects at the expense of greater acute anxiety and potentially greater adverse effects. Thus, a method of dosing psilocybin at high to very high doses is appropriate for individuals experienced with lower doses of psilocybin or other psychedelics and aiming for a more intense and ego-dissolving experience but also ready to risk experiencing greater anxiety when dealing with this state. Ego-dissolution as experience may be therapeutic in some indications namely in individuals with severe pain disorders, with cancer and/or in palliative care with the goal of being free of pain or at least not realizing somatic pain and the presence of the body or feeling out of the body during this experience. Ego-dissolution can also be a therapeutic experience in other disorders including personality disorder (narcissistic personality disorder) or as needed by psychiatric indications. The present invention allows for the use of high doses of psilocybin while at the same time reducing negative effects including bad drug effects, anxious ego dissolution, anxiety, autonomic stimulation, and adverse effects as shown in EXAMPLE 1.

Psilocybin or related compounds of the present invention are administered and dosed in accordance with good medical practice, considering the clinical condition of the individual patient, the site and method of administration, scheduling of administration, patient age, sex, body weight and other factors known to medical practitioners. The pharmaceutically "effective amount" for purposes herein is thus further determined by such considerations as are known in the art. The amount must be effective to achieve improvement including but not limited to more rapid recovery, or improvement or elimination of symptoms and other indicators as are selected as appropriate measures by those skilled in the art.

In the method of the present invention, the compounds of the present invention can be administered in various ways. It should be noted that they can be administered as the compound orally as done in the example study and can be administered alone or as an active ingredient in combination with pharmaceutically acceptable carriers, diluents, adjuvants, and vehicles. The compounds can be administered orally, subcutaneously or parenterally including intravenous, transcutaneous, intramuscular, and intranasal administration. The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material not reacting with the active ingredients of the invention.

The doses can be single doses or multiple doses or a continuous dose over a period of several hours.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

To summarize, the specific uses of psilocybin and its analogs in the context of substance assisted psychotherapy in humans within the present invention are described as follows: Psilocybin given in combination with an antidepressant can be used to assist and enhance any type of psychotherapy. A psilocybin-assisted session can be used after conducting psychotherapy sessions in a person without psilocybin. A psilocybin-assisted session can be integrated in non-substance assisted psychotherapy. Psilocybin can also be used after other psychedelics such as LSD or the empathogen MDMA have been used in a patient and resulted in insufficient responses or adverse effects.

Psilocybin in combination with an antidepressant such as escitalopram can also be preferred in some patients with expected adverse effects. For example, it may not be desired to use psilocybin without an antidepressant or other substances such as MDMA in some patients with an increased risk for specific adverse effects such as in patients with cardiovascular disease of arterial hypertension or genetic disorders such as malignant hyperthermia.

The individual can be treated with psilocybin or another psychedelic if already treated with an antidepressant because the antidepressant cannot be stopped (due to risk of relapse of depression or relapse of anxiety or relapse of any other disorder for which the individual is treated with the antidepressant or fear of withdrawal). The individual can also newly be treated with an antidepressant such as escitalopram just for a few days (1-30) before a planned administration of psilocybin because establishing an antidepressant treatment is clinically desired or because it is specifically used to reduce adverse effects of the planned psilocybin administration.

The antidepressant pretreatment, for example escitalopram, can also specifically be used before the administration of a psychedelic such a psilocybin to reduce adverse effects of the psychedelic such as acute anxiety or negative subjective drug effects and thereby enhance the potential positive long-term therapeutic effects of the psychedelic.

Example 1: Effects of Serotonin Transporter Inhibition on the Subjective Response to Psilocybin in Healthy Subjects Psilocybin is a classic serotonergic hallucinogen. It was discovered in Basel by Hofmann in 1958. Psilocybin is investigated in the treatment of depression (Carhart-Harris et al., 2021; Carhart-Harris et al., 2018; Carhart-Harris et al., 2016; Davis et al., 2021), anxiety (Griffiths et al., 2016; Ross et al., 2016), and substance use (Garcia-Romeu et al., 2014). In particular, there are high hopes of using psilocybin in patients with treatment resistant major depression and pharmaceutical companies are currently planning phase 2 studies (Carhart-Harris & Goodwin, 2017; Nichols et al., 2017; Rucker et al., 2018).

Psilocybin is a prodrug which is activated to psilocin within the body (Hasler et al., 1997; Passie & Halpern, 2014; Passie et al., 2002). The mechanism of action of psilocin primarily involves an interaction with the serotonin $5-HT_{2A}$ receptor, similar to LSD (Liechti, 2017). Consistently, the alterations of mind induced by psilocybin in humans can be reduces by pretreatment with a serotonin $5-HT_2$ receptor antagonist (Vollenweider et al., 1998) and subjective effects are associated with $5-HT_2$ occupancy (Madsen et al., 2019). Positive acute effects of psilocybin are associated with the long-term therapeutic response (Griffiths et al., 2016; Roseman et al., 2017; Ross et al., 2016) and are therefore thought to contribute to the therapeutic effects of psilocybin (Ly et al., 2018; Rucker et al., 2018). However, psilocybin and other psychedelics produce also additional effects including mainly neuroplasticity including increases in brain-derived neurotrophic factor (BDNF) (Holze et al., 2021; Hutten et al., 2020) that may be therapeutically relevant (Ly et al., 2018; Yang et al., 2020).

Patients with depression are usually treated with an antidepressant. SERT inhibitors also called selective serotonin reuptake inhibitors (SSRIs) are considered the first-line antidepressants (Koenig & Thase, 2009). The use of SSRIs is very common. Approximately one in nine Americans reported taking at least one antidepressant drug in the past month (Pratt Laura A., 2017). SSRIs acutely increase 5-HT levels in the synapses in the brain, however, the mood-elevating effects occur only after several weeks of repeated daily treatment and are likely associated with adaptive changes of the brain. For example, chronic administration of antidepressants has been shown to decrease the number of $5-HT_2$ receptors in various brain regions due to receptor downregulation (Bonson et al., 1996; de Montigny et al., 1990). Because the $5-HT_{2A}$ receptor is the primary target of psilocin, SSRIs may reduce the effects of psilocybin or other psychedelics. Reportedly, other antidepressants such as the monoamine inhibitor (MAOI) tranylcypromine or nialamide which are not used anymore reduced the typical LSD effects (Bonson & Murphy, 1996; Grof & Dytrych, 1965; Maracek et al., 1968) while another MAOI (isocarboxazid) reportedly had no effect (DeMaar et al., 1960). The SSRIs fluoxetine or sertraline also reportedly reduced LSD effects in case reports or retrospective studies (Bonson et al., 1996; Bonson & Murphy, 1996; Strassman, 1992). Importantly, all these studies were not placebo-controlled and evaluated the effects of LSD only. However, it was assumed that antidepressants reduce the response to psychedelics and should be stopped in clinical trials investigating therapeutic effects of LSD or psilocybin. Specifically, study participants were free of concomitant anti-depressants for two weeks prior to randomization and for the duration of the study (Carhart-Harris et al., 2018; Ross et al., 2016) or medications affecting the serotonin system were stopped at least 5 half-lives before psilocybin administration (Griffiths et al., 2016) or study inclusion (Davis et al., 2021) in clinical trials using psilocybin in patients with depression and/or anxiety. This means that research trials performed with psilocybin stopped any antidepressant treatment long before the psilocybin administration. Similarly, patients administered with LSD within the Swiss compassionate use program pause any SSRI treatment typically for 5 days before their LSD treatment sessions. However, whether this is necessary is unclear and it may be problematic in many patients needing the antidepressant treatment or suffering from withdrawal when stopping it.

The goal of the present invention was therefore to develop a treatment method combining the antidepressant treatment with psilocybin and to specifically test this in an application in humans within a valid clinical trial in this EXAMPLE.

The primary goal of the present EXAMPLE is to test in a clinical study whether the psilocybin response is altered following treatment with escitalopram. The $5-HT_{2A}$ receptor gene ($5HTR_{2A}$) expression is also tested in blood as a marker of the central nervous system (CNS) receptor expression after escitalopram and placebo treatment. Furthermore, the study provides key information on the drug-drug interaction of the SSRI escitalopram and psilocin. This is critical since patients under chronic SSRI treatment for depression are typically among those considered for psilocybin treatment. Because the acute response to psilocybin has been shown to predict its long-term therapeutic response it is critical to know whether the SSRI treatment alters the response to psilocybin administration. Psilocybin and escitalopram can also interact pharmacokinetically. Escitalopram is metabolized via CYP2C19, 2C6 and 3A4. Escitalopram also slightly inhibits CYP2C19 and 2D6 function (FDA, 2017; Swissmedic, 2020). The metabolism of psilocin is not known. The present example provides information on pharmacokinetic interactions between escitalopram and psilocybin. Thus, plasma levels of psilocybin were repeatedly measured after its administration to evaluate its pharmacokinetics after escitalopram and placebo.

Study Methods

Study design: A double-blind, cross-over design was used with two conditions. Conditions were 1) pretreatment with escitalopram 10 mg for 7 days, followed by escitalopram 20 mg for another 7 days with the last dose given on the study day and administration of 25 mg psilocybin 2 hours later. 2) Pretreatment with placebo for 14 days with the last administration on the study day and administration of 25 mg psilocybin 2 hours later. Treatment order was random and counterbalanced. Between the 14 days pretreatment and the study day, there were at least 2 days washout until the next pretreatment phase began. The study did not include a placebo condition for the psilocybin administration because the effects of psilocybin vs. placebo have been extensively investigated and we primarily wanted to test the effect of the pretreatment on the response to psilocybin.

Inclusion criteria: Age between 25 and 65 years; Understanding of the German language. Understanding the procedures and the risks that are associated with the study. Participants must be willing to adhere to the protocol and sign the consent form. Participants must be willing to refrain from taking illicit psychoactive substances during the study. Participants must be willing to drink only alcohol-free liquids and no coffee, black or green tea, or energy drink after midnight of the evening before the study session, as well as during the study day. Participants must be willing not to drive a traffic vehicle or to operate machines within 24 hours after substance administration. Women of childbearing potential must have a negative pregnancy test at the beginning of the study. Pregnancy tests are repeated before each study session. Women of childbearing potential must be willing to use double-barrier birth control.

Exclusion criteria: Chronic or acute medical condition, including a history of seizures. Current or previous major psychiatric disorder (e.g. psychotic disorders, mania/hypomania, anxiety disorders, and substance abuse). Psychotic disorder in first-degree relatives, not including psychotic disorders secondary to an apparent medical reason, e.g. brain injury, dementia, or lesions of the brain. Illicit substance use (with the exception of *cannabis*) more than 10 times or any time within the previous two months. History of an angle closure glaucoma. Pregnant or nursing women. Participation in another clinical trial (currently or within the last 30 days). Use of medications that may interfere with the effects of the study medications (any psychiatric medications and any medication with known pharmacokinetic or pharmacodynamic interactions with escitalopram). A corrected QT time (QTc), calculated by Bazett's formula, of over 450 milliseconds in males and over 470 milliseconds in females. Tobacco smoking (>10 cigarettes/day). Consumption of alcoholic drinks (>10 drinks/week). Bodyweight <45 kg.

Figure 2:
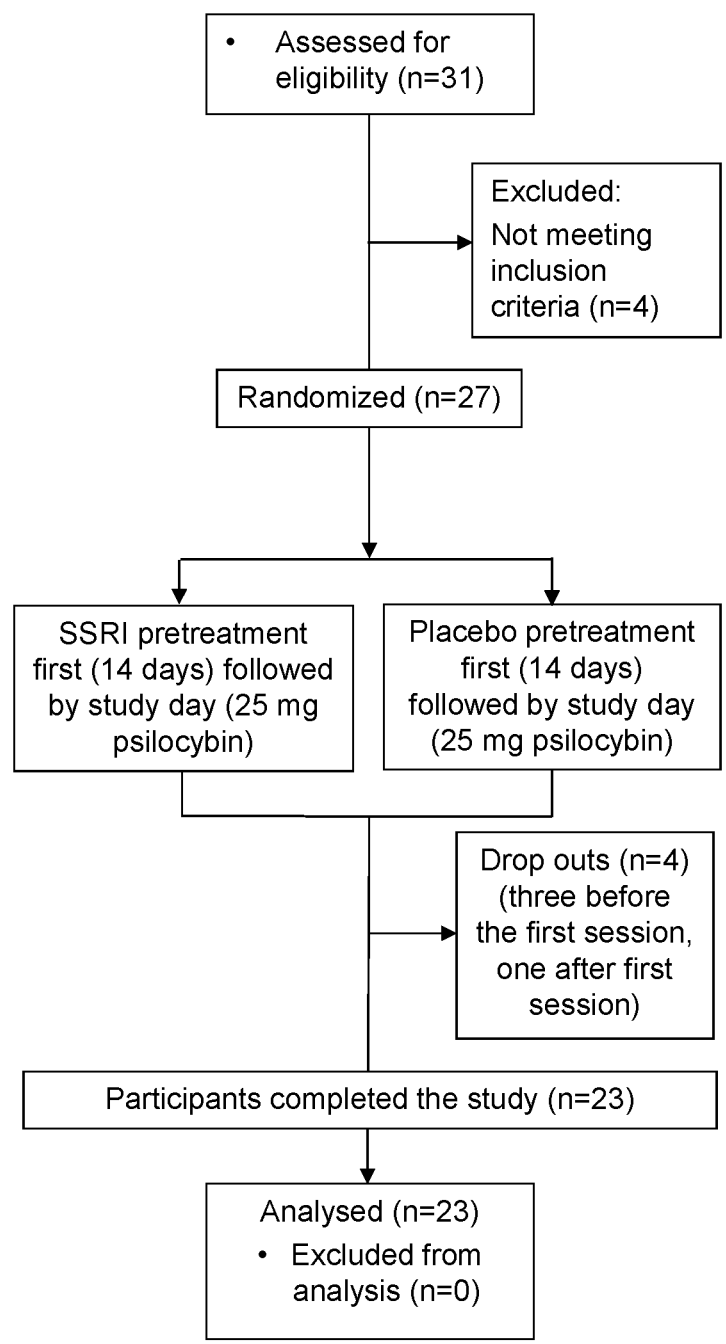
FIG. 2 is a schematic of the study design and participant flow.

Participants: The study was conducted at the University Hospital Basel. Subjects were recruited by an advertisement on the home page of the University of Basel. Twenty-seven participants were randomized (FIG. 2). Four subjects stopped participation before the first treatment session and one subjects stopped after one treatment session resulting in a total of twenty-three who completed both sessions and the entire study. These twenty-three healthy subjects (11 women, 12 men) were 34±10 years old [mean±SD]; range 25-55 years. Mean body weight was 70 kg, with 63 kg in women and 77 kg in men, respectively. Six participants had previously used psilocybin-containing mushrooms (1-4 times), eight had used 3,4-Methylenedioxymethamphetamine (MDMA) (1-5 times). Six women used hormonal contraception.

Study procedures: Subjects took part in a 2-hour screening session, two 9.5-hour test sessions where the psilocybin was administered and a 1-hour end-of-study visit. The subjects were informed about the study both verbally and by the approved written consent form regarding the altered state of consciousness, the study procedures and associated risks. The investigator and the subject both personally signed and dated the consent form as confirmation of consent. Subjects were screened using a semi-structured clinical interview for DSM-IV (Diagnostic and Statistical Manual Version 4) (Wittchen et al., 1997) to exclude those with a personal or family (first-degree relative) axis I major psychiatric disorder (acute or past) or a history of illicit drug dependence. Axis I major psychiatric disorders included also addiction disorders. The sessions were conducted in a calm standard hospital room. Only one research subject and one investigator were present during the test sessions. The test sessions began at 9 AM. The subjects then underwent baseline measurements. The final dose of escitalopram or placebo was administered at 9:00 AM. Psilocybin was administered at 11:00 AM. The outcome measures were repeatedly assessed for 7 hours. The subjects were under constant supervision by an investigator until 6 PM. Thus, the subjects were never alone during the 7 hours after drug administration. The subjects were sent home at 6:30 PM.

Psilocybin drug product and dose: Psilocybin was prepared as capsules containing 5 mg of analytically pure psilocybin dihydrate (ReseaChem GmbH, Burgdorf, Switzerland) and mannitol filler. Formulations plus matching placebos were prepared by a GMP facility (Apotheke Dr. Hysek, Biel, Switzerland) according to GMP guidelines. Escitalopram was used as the marketed product (Cipralex, 10 mg) and encapsuled with opaque capsules for blinding purposes using mannitol as filler. Similar placebo was prepared containing a mannitol tablet and mannitol filler. Randomization, packaging, labelling, and quality control (QC) including stability tests were handled by the GMP facility. Subjects and study personnel involved in supervising the session were blinded to treatment order that was balanced.

The present study used 25 mg of psilocybin. A similar dose has also been used in patients (Carhart-Harris et al., 2016; Griffiths et al., 2016; Nichols, 2016)

Psychometric Assessment

Subjective Effects Questionnaire (Visual Analog Scales, VAS): VAS was repeatedly used to assess subjective alterations in consciousness over time. Single scales were presented as 100 mm horizontal lines marked with "not at all" on the left and "extremely" on the right. The following VAS items were used: "any drug effect", "good drug effect", "bad drug effect", "drug liking", "drug high", "stimulated", "fear", "happy", "content", "trust", "talkative", "perception of time", "open", "concentration", "speed of thinking", "feeling close to others", "wanting to be hugged", "wanting to hug someone", "desire to be alone", "desire to be with others", and "ego dissolution". The VASs were presented as 100-mm horizontal lines (0-100%), marked from "not at all" on the left to "extremely" on the right. Some VASs were bidirectional (±50%). Marked from "not at all" on the left (−50), to "normal" in the middle (0), to "extremely" on the right (+50). Scales were administered before and at 0, 0.25, 0.5, 0.75, 1, 1.5, 2, 2.5, 3, 4, 5, 6 and 7 hours after psilocybin administration.

The 60-item Adjective Mood Rating Scale (AMRS) (Janke & Debus, 1978) was administered before and 2, 3, 5, and 7 hours after psilocybin administration.

Figure 17:
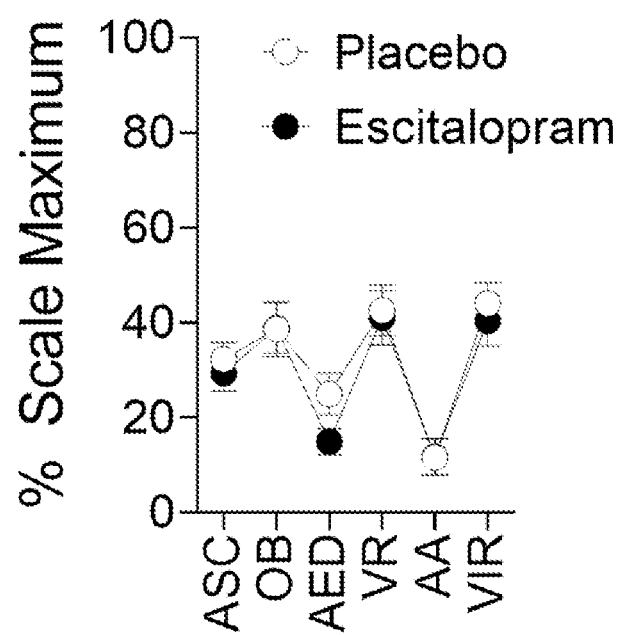
FIG. 17 is a graph showing effects of psilocybin on the 5-Dimensions of Altered States Scale main scales after escitalopram and placebo pretreatment.
Figure 18:
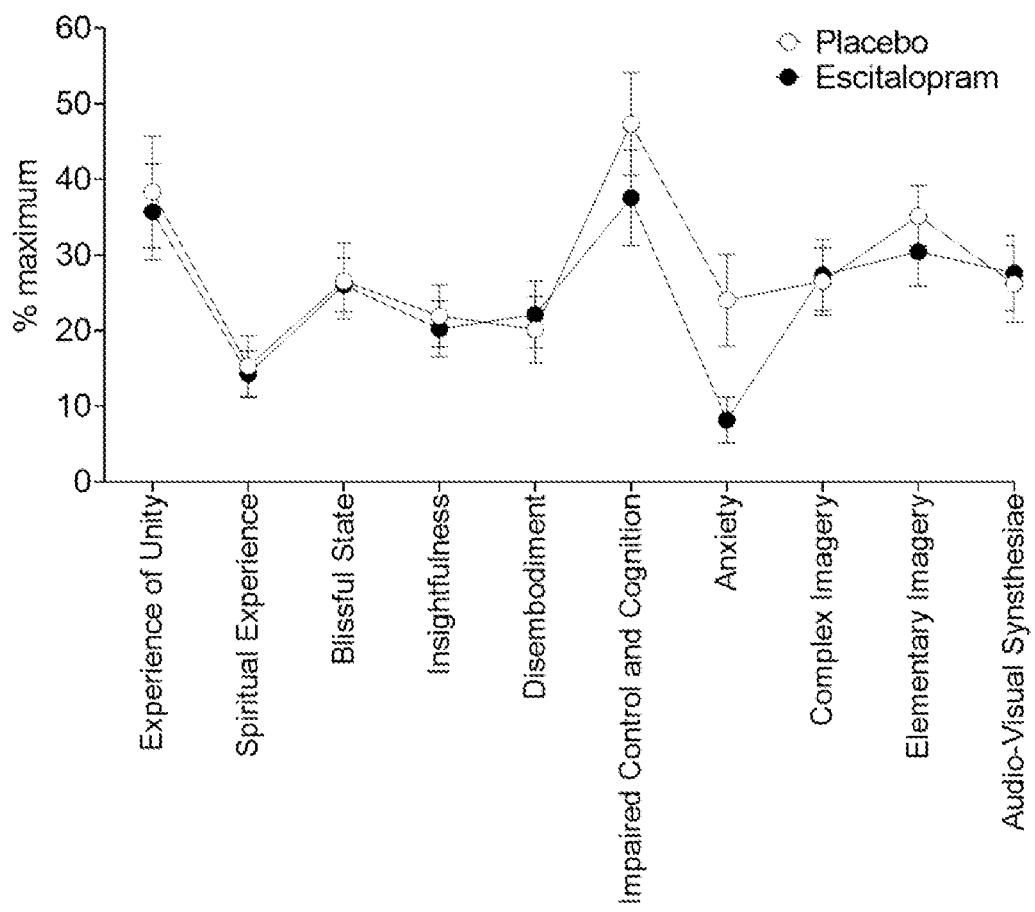
FIG. 18 is a graph showing effects of psilocybin on the 5-Dimensions of Altered States Scale subscales after escitalopram and placebo pretreatment.

5-Dimensional Altered States of Consciousness (5D-ASC): The 5-dimensional Altered States of Consciousness (5D-ASC) Scale is a visual analog scale consisting of 94 items (Dittrich, 1998; Studerus et al., 2010). The instrument contains five main scales (FIG. 17) and 11 newer subscales (FIG. 18) assessing mood, anxiety, derealization, depersonalization, changes in perception, auditory alterations, and reduced vigilance. The scale is well-validated (Studerus et al., 2010). The total ASC score is the sum of the three main dimensions/scales Oceanic Boundlessness (OB), Anxious Ego Dissolution (AED) and Visionary Restructuralization (VR). There are two additional main scales measuring Auditory Alterations (AA) and Vigilance Reduction (VIR) (FIG. 17). The 5D-ASC scale was administered once at the end of the session and subjects were instructed to retrospectively rate peak alterations that have been experienced during the study session. Each item of the scale is scored on a 0-100 mm VAS. The attribution of the individual items to the subscales of the 5D-ASC was analyzed according to (Dittrich, 1998; Studerus et al., 2010) and as shown in FIG. 18. The scale was be administered once at the end of each test session.

Mystical experiences were assessed using the German version (Liechti et al., 2017) of the 100-item States of Consciousness Questionnaire (SOCQ) (Griffiths et al., 2006) that includes the 43-item and newer 30-item MEQ (MEQ43 (Griffiths et al., 2006) and MEQ30 (Barrett et al., 2015)). The scale was be administered once at the end of each test session.

Autonomic measures: Blood pressure, heart rate, and body temperature were recorded at baseline and repeatedly throughout the session. Blood pressure (systolic and diastolic) and heart rate were measured with an automatic oscillometric device. Body temperature was measured with an ear thermometer as previously described in detail (Hysek et al., 2010). Measures were taken before and at 0, 0.25, 0.5, 0.75, 1, 1.5, 2, 2.5, 3, 4, 5, 6 and 7 hours after psilocybin administration.

Adverse effects (list of complaints): The list of complaints (LC) consists of 66 items offering a global score measuring physical and general discomfort (Zerssen, 1976). This scale yields a total adverse effects score and reliably measures physical and general discomfort. The LC list was administered 7 hours after administration of the drug with reference to complaints throughout the entire session.

Psychedelics can induce neuroregeneration (Ly et al., 2018). Plasma BDNF levels are a possible biomarker for neurogenesis (Haile et al., 2014). Psychedelics increase BDNF (Holze et al., 2021; Hutten et al., 2020) and higher BDNF levels were associated with lower depression ratings after administration of psychedelics (de Almeida et al., 2019). Plasma BDNF levels were measured at baseline and 4 and 7 hours after drug administration using the Biosensis Mature BDNF Rapid ELISA Kit (Thebarton, Australia) (Akimoto et al., 2019).

Gene expression: Blood samples were collected before the psilocybin administration using the PAXgene™ Blood RNA system (Becton Dickinson, Heidelberg, Germany). Samples were incubated for 2 h at room temperature, followed by freezing at −80° C. until further processing. Total RNA was prepared using the PAXgene™ Blood RNA Kit 50 (PreAnalytiX, Qiagen, Hilden, Germany). Total RNA samples were spectrophotometrically scanned (260 and 280 nm; NanoVue, GE Healthcare Life Sciences, Glattbrugg, Switzerland). A260 was used for RNA quantification. The A260/A280 ratio was >1.9, excluding relevant protein contamination. RNA quality was also measured using Experion RNA chips (BioRad, Hercules, CA, USA) providing the RNA quality indicator (RQI>7). Quantitative real-time polymerase chain reaction (PCR) was performed for the HTR2A and SCL6A4 genes and four additional reference genes (ACTB, ALAS1, RPL13A, and RRN18S) as described previously (Grunblatt et al., 2009). Total RNA (500 ng) from each sample was reverse transcribed using the iScript cDNA synthesis kit (BioRad, Hercules, CA, USA). Each amplification was performed in a total volume of 10 µl that contained 5 µl of the QuantiFast SYBR Green PCR kit (Qiagen, Hilden, Germany) and the specific PrimerAssay (Qiagen, Hilden, Germany). The PCR conditions were run on a CFX384 device (BioRad, Hercules, CA, USA) according to manufacturer's manual, with the exception of HTR2A primers, in which annealing occurred at 56° C. according to a gradient analysis (Qiagen, Hilden, Germany). A melting-point analysis was conducted for each assay to confirm the specificity of the PCR products. All of the PCR reactions were run in triplicate.

Plasma drug concentrations: Blood was collected into lithium heparin tubes at 0, 0.25, 0.5, 0.75, 1, 1.5, 2, 2.5, 3, 4, 5, 6 and 7 hours after psilocybin administration. The blood samples were immediately centrifuged, and the plasma was subsequently stored at −80° C. until analysis.

Psilocybin plasma concentrations were analyzed using a validated ultra-high-performance liquid chromatography tandem mass spectrometry method as described previously (Kolaczynska et al., 2021). All samples were reanalyzed after deglucuronidation with Escherichia coli β-glucuronidase (Kolaczynska et al., 2021). This allows to determine the concentrations of unconjugated psilocin and of psilocin glucuronide which corresponds to the difference between samples that were incubated with and without glucuronidase.

Pharmacokinetic analyses and pharmacokinetic-pharmacodynamic modeling: Pharmacokinetic parameters were estimated using non-compartmental methods in Phoenix WinNonlin 6.4 (Certara, Princeton, NJ, USA) as described previously in detail (Holze et al., 2019).

Data analysis: Peak (Emax and/or Emin) or peak change from baseline (ΔEmax) values were determined for repeated measures. The values were then analyzed using paired T-tests using Statistica 12 software (StatSoft, Tulsa, OK, USA). The criterion for significance was $p<0.05$.

Results

Figure 6A:
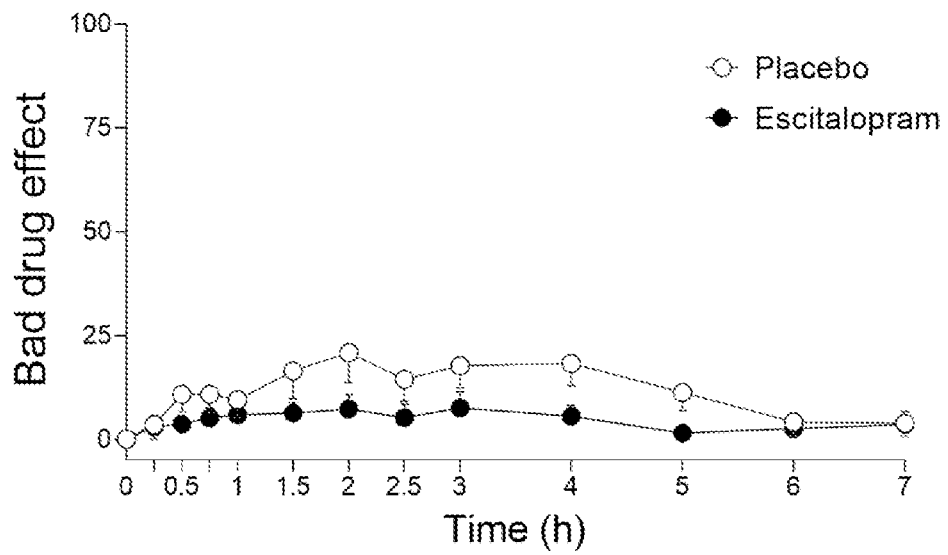
FIG. 6A is a graph showing subjective bad drug effect and FIG. 6B is a graph showing fear induced by psilocybin after escitalopram and placebo pretreatment.
Figure 6B:
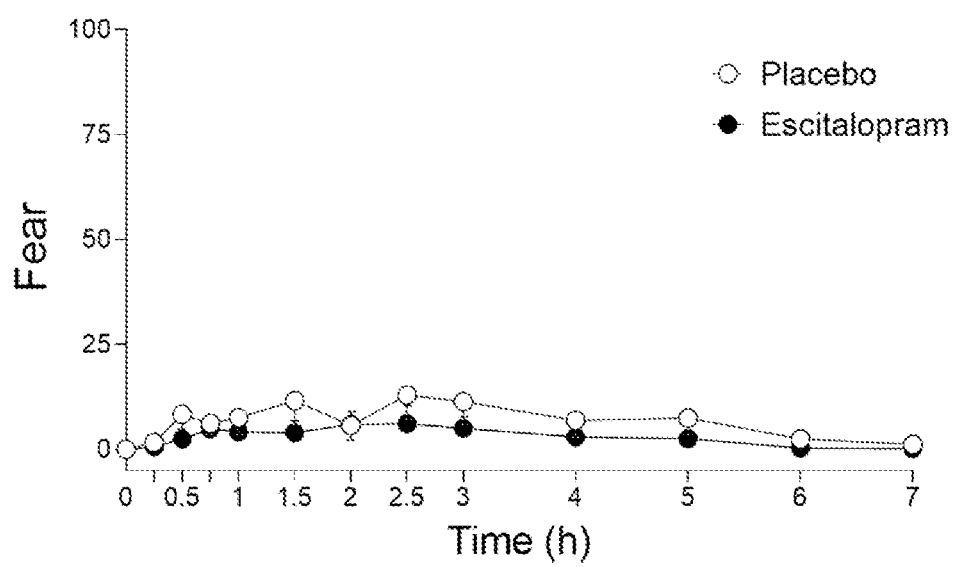
Figure 7A:
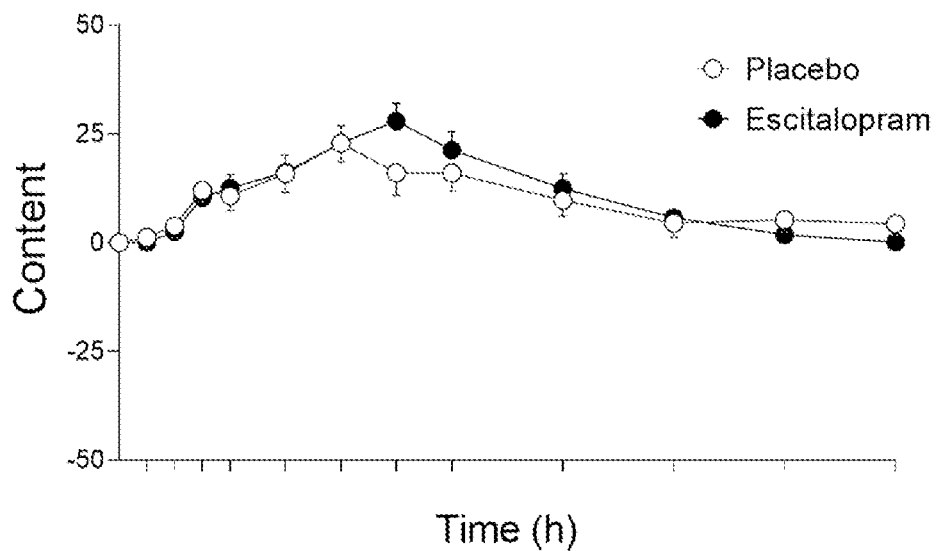
FIG. 7A is a graph showing feeling content and FIG. 7B is a graph showing trust induced by psilocybin after escitalopram and placebo pretreatment.
Figure 7B:
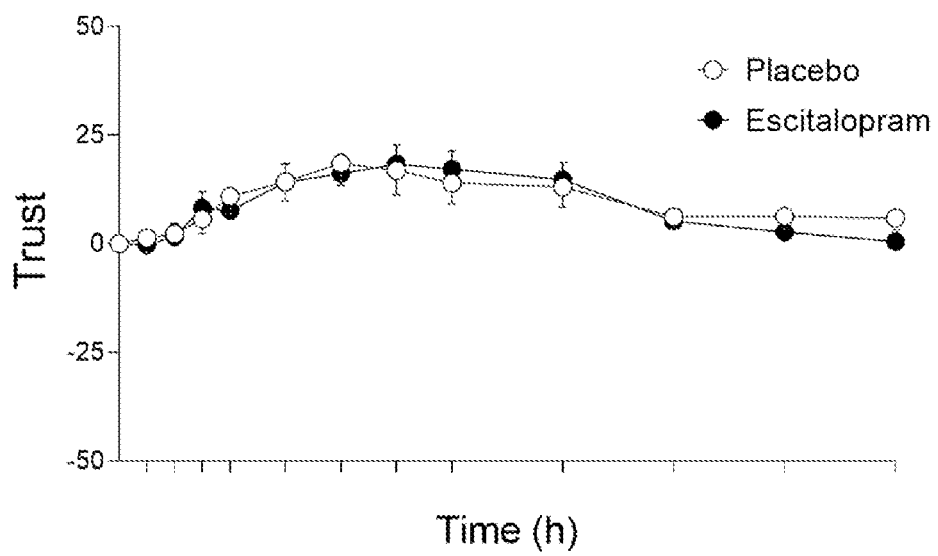
Figure 8A:
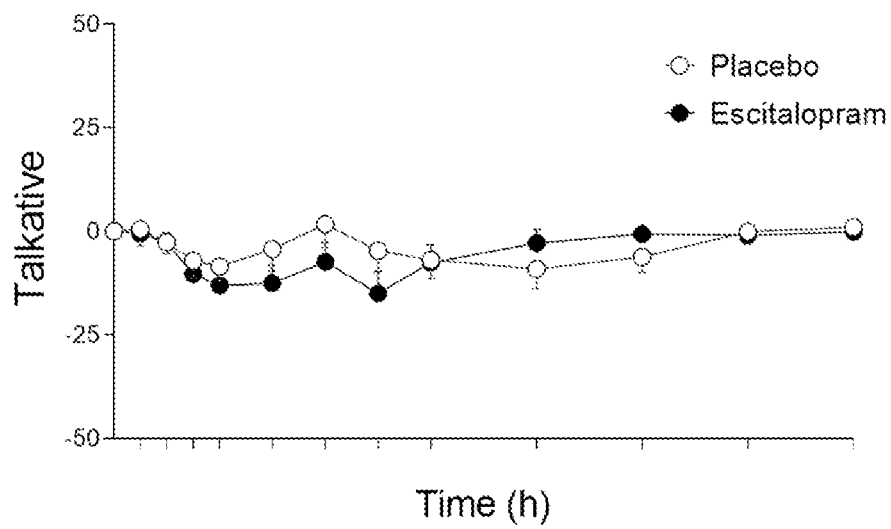
FIG. 8A is a graph showing feeling talkative and FIG. 8B is a graph showing changes in perception of time induced by psilocybin after escitalopram and placebo pretreatment.
Figure 8B:
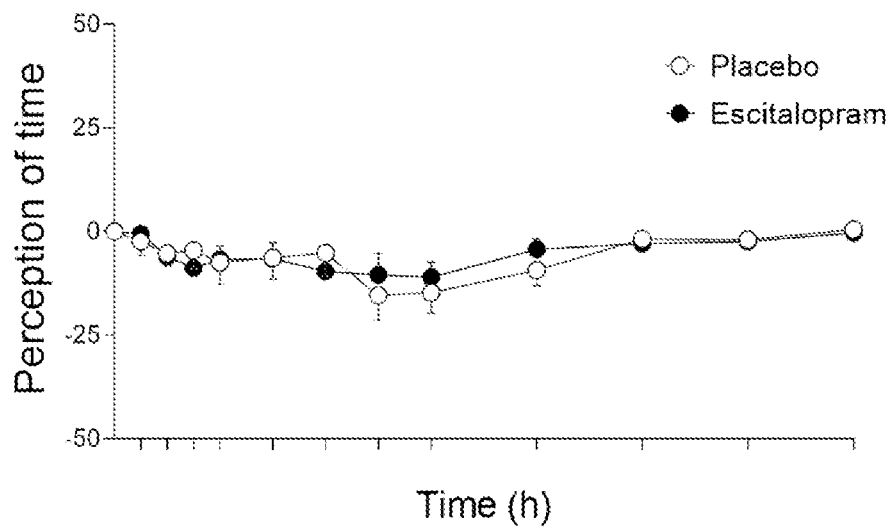
Figure 9A:
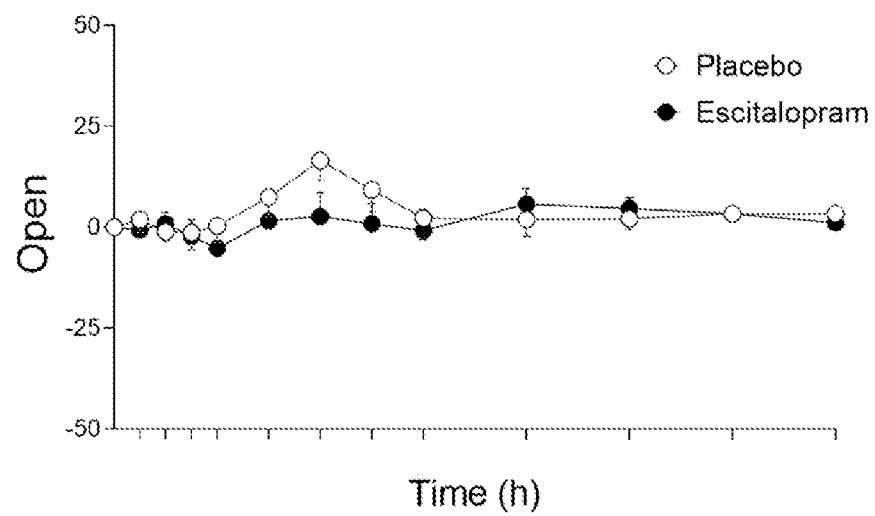
FIG. 9A is a graph showing feeling open and FIG. 9B is a graph showing subjective concentration induced by psilocybin after escitalopram and placebo pretreatment.
Figure 9B:
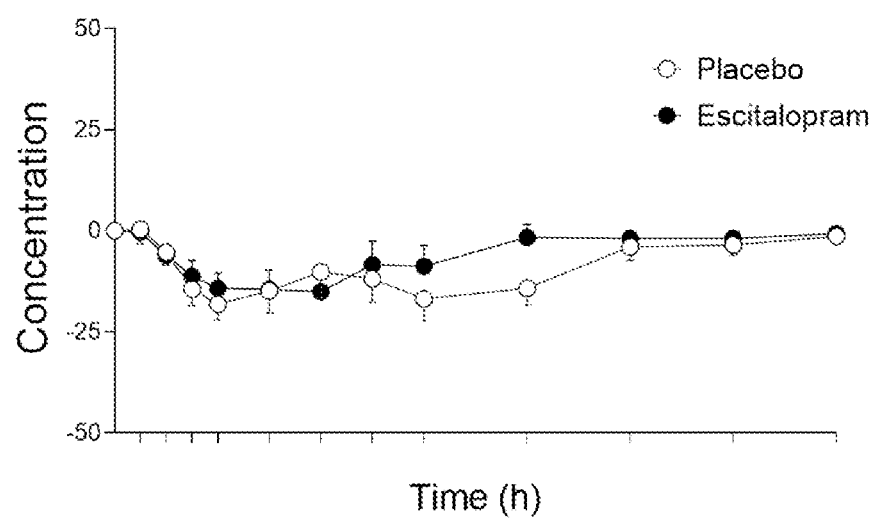
Figure 10A:
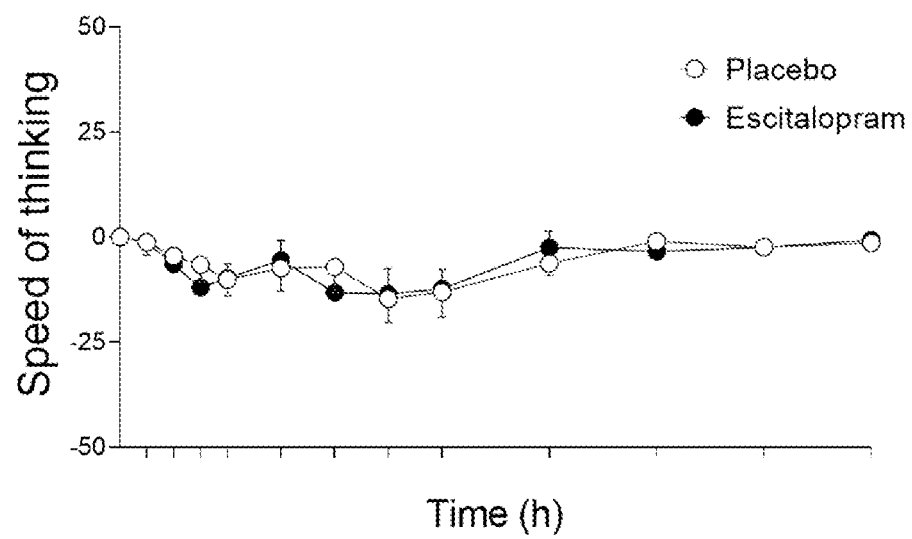
FIG. 10A is a graph showing subjective speed of thinking and FIG. 10B is a graph showing feeling close to others induced by psilocybin after escitalopram and placebo pretreatment.
Figure 10B:
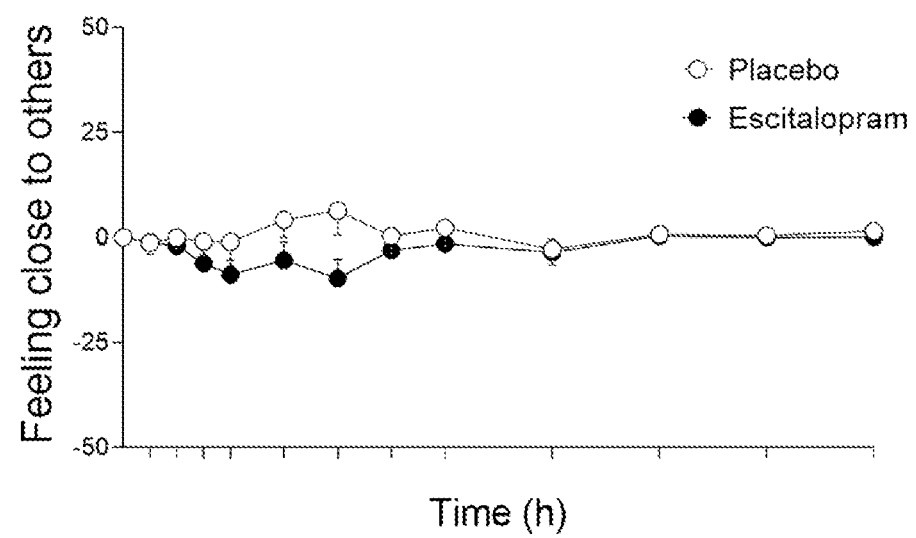
Figure 11A:
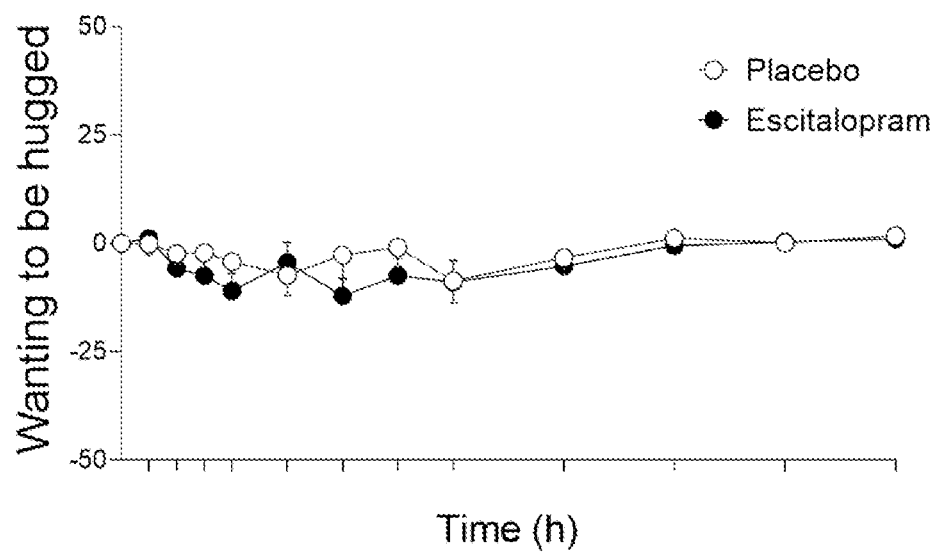
FIG. 11A is a graph showing wanting to be hugged and FIG. 11B is a graph showing wanting to hug someone induced by psilocybin after escitalopram and placebo pretreatment.
Figure 11B:
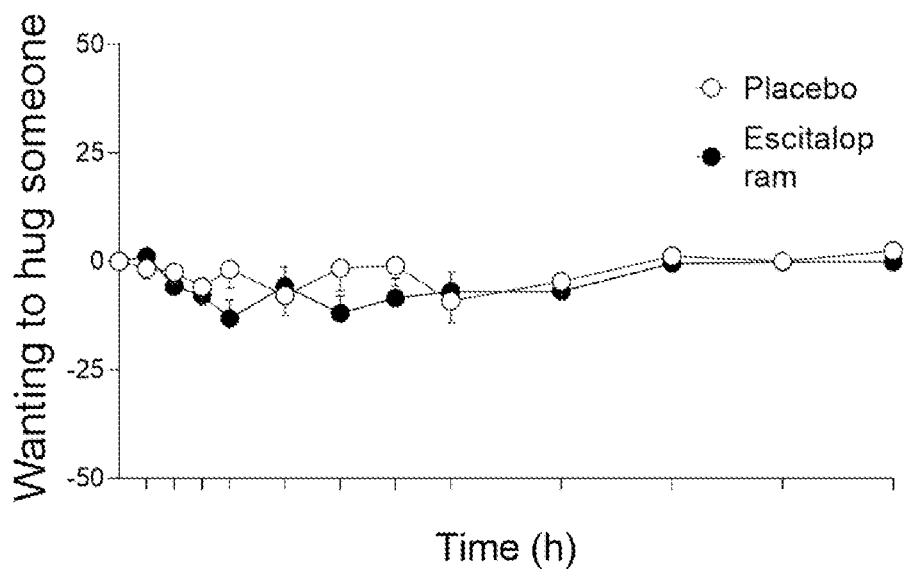
Figure 12A:
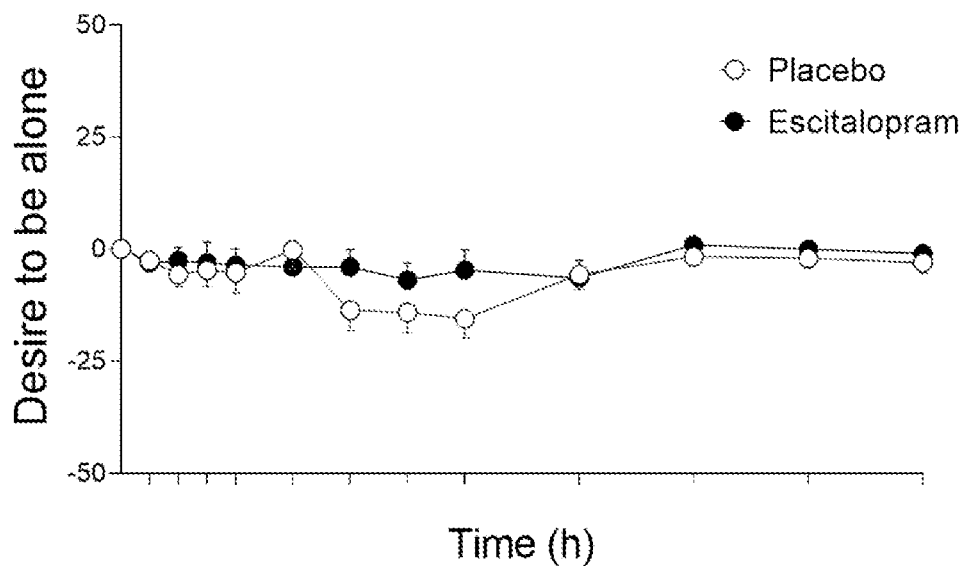
FIG. 12A is a graph showing desire to be alone and FIG. 12B is a graph showing desire to be with others induced by psilocybin after escitalopram and placebo pretreatment.
Figure 12B:
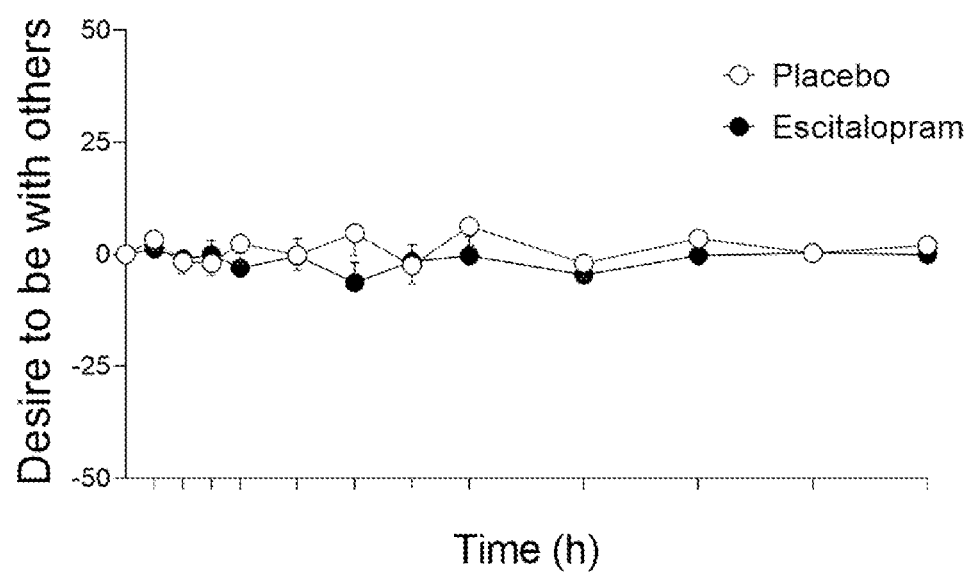
Figure 13:
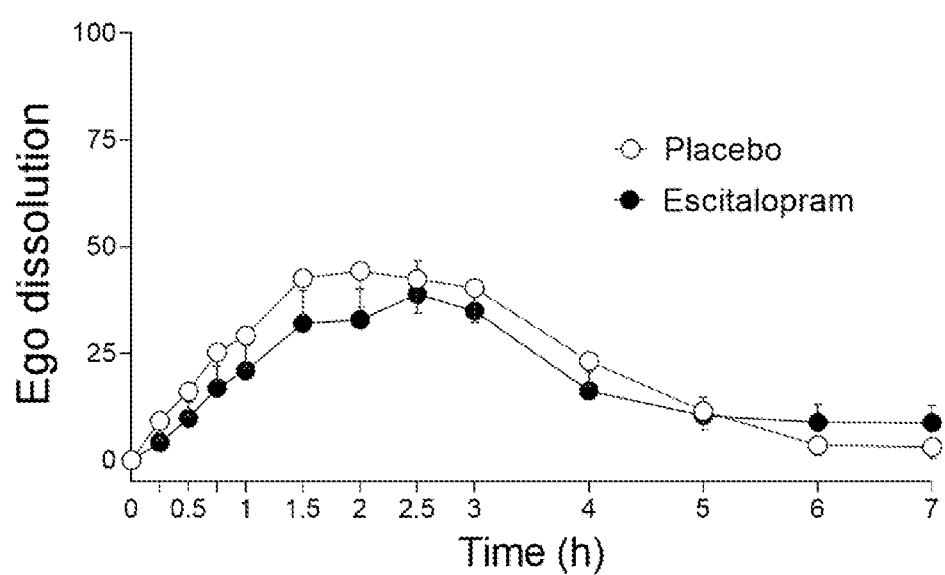
FIG. 13 is a graph showing ego dissolution induced by psilocybin after escitalopram and placebo pretreatment.
Figure 14A:
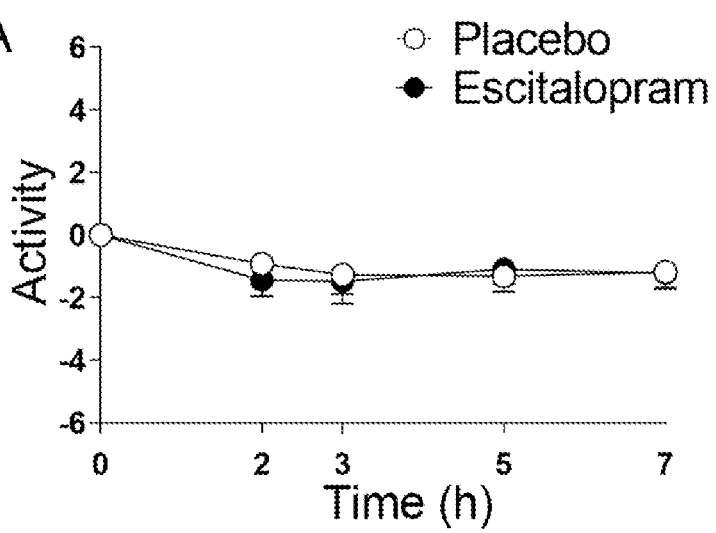
FIG. 14A is a graph showing activity.
Figure 14B:
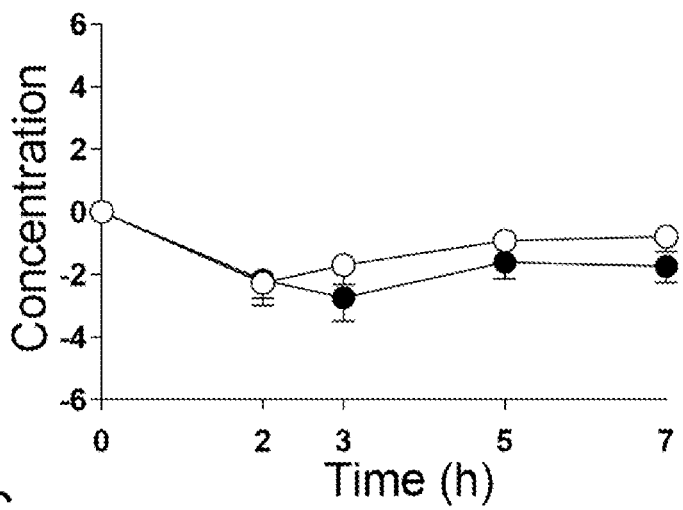
FIG. 14B is a graph showing concentration.
Figure 14C:
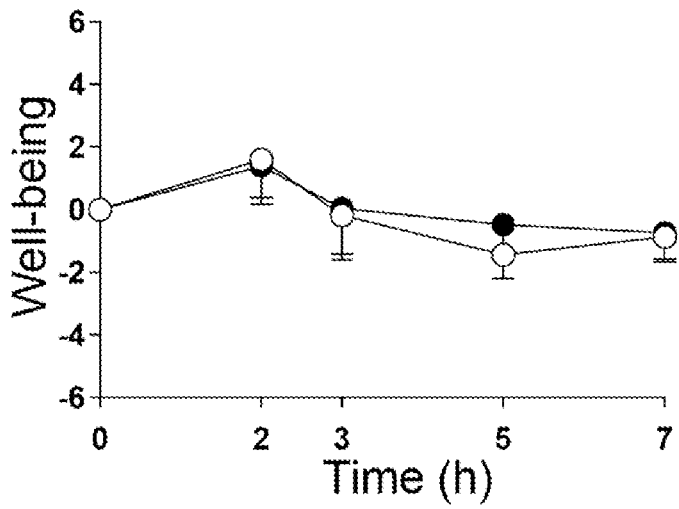
FIG. 14C is a graph showing well-being induced by psilocybin after escitalopram and placebo pretreatment.
Figure 15A:
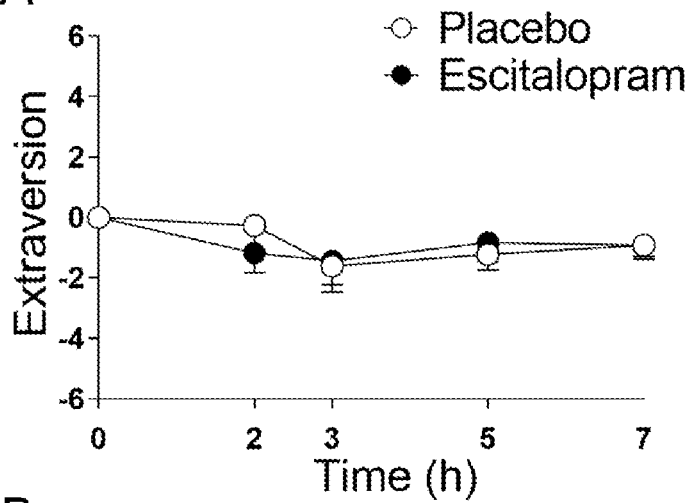
FIG. 15A is a graph showing extraversion.
Figure 15B:
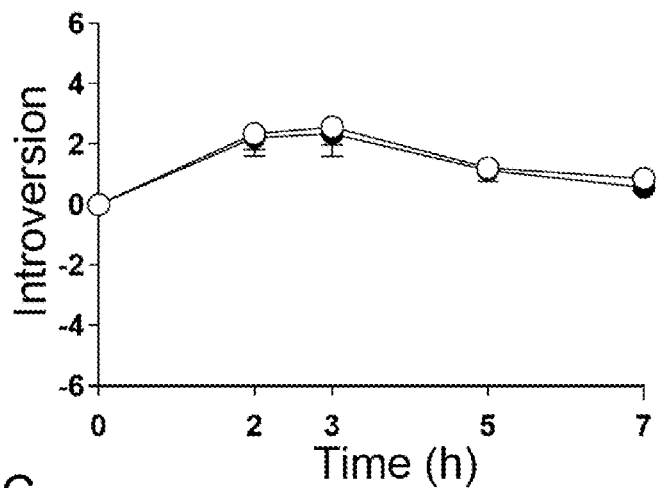
FIG. 15B is a graph showing introversion.
Figure 15C:
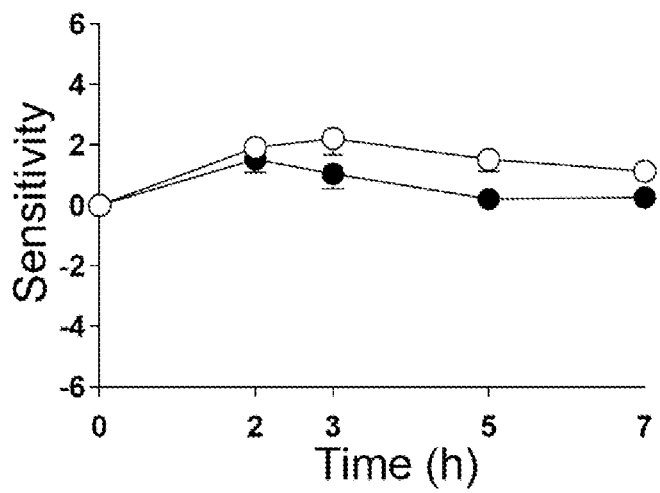
FIG. 15C is a graph showing sensitivity induced by psilocybin after escitalopram and placebo pretreatment.
Figure 19:
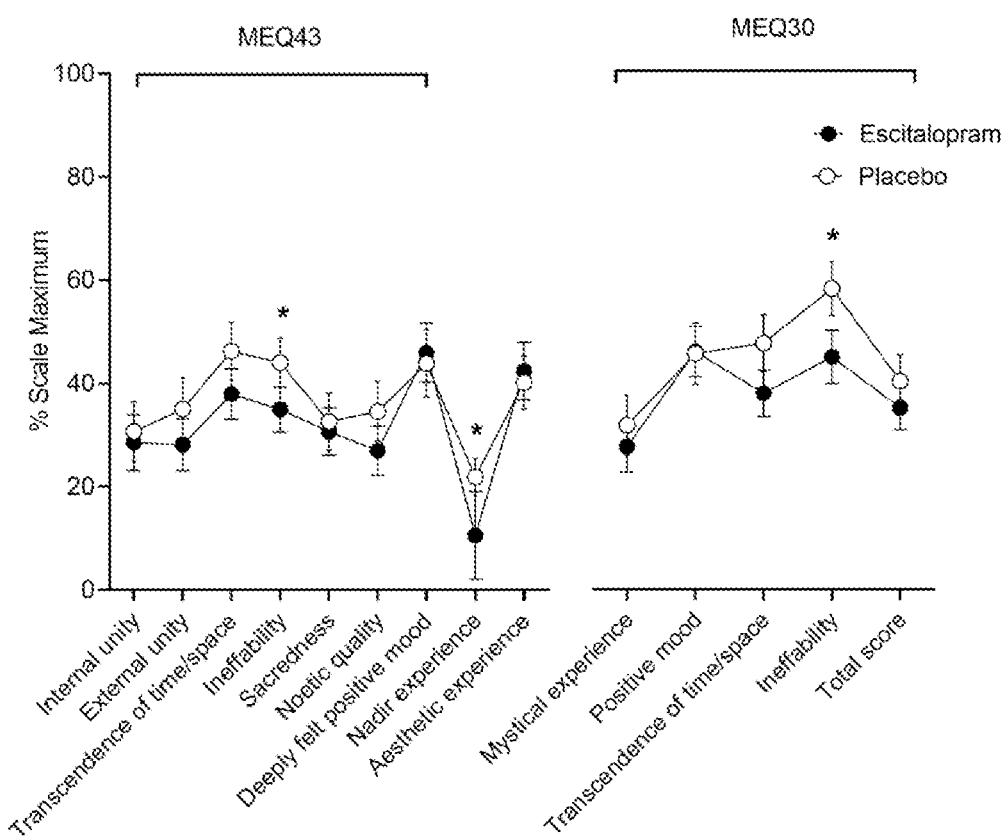
FIG. 19 is a graph showing effects of psilocybin on the Mystical Experience Questionnaire (MEQ30 and MEQ43) after escitalopram and placebo pretreatment.
Figure 20A:
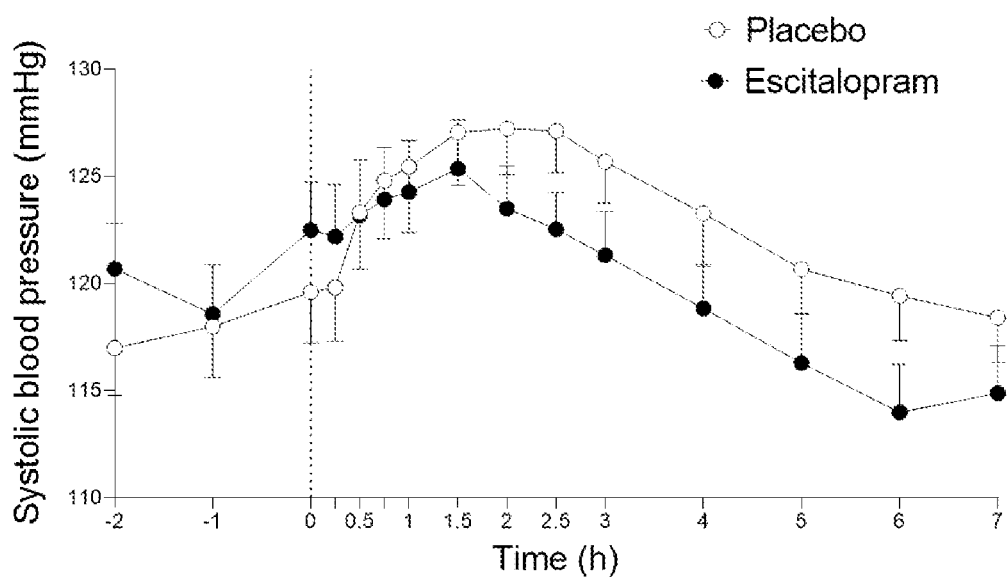
FIG. 20A is a graph showing effects of psilocybin on systolic blood pressure and FIG. 20B is a graph showing diastolic blood pressure after escitalopram and placebo pretreatment.
Figure 20B:
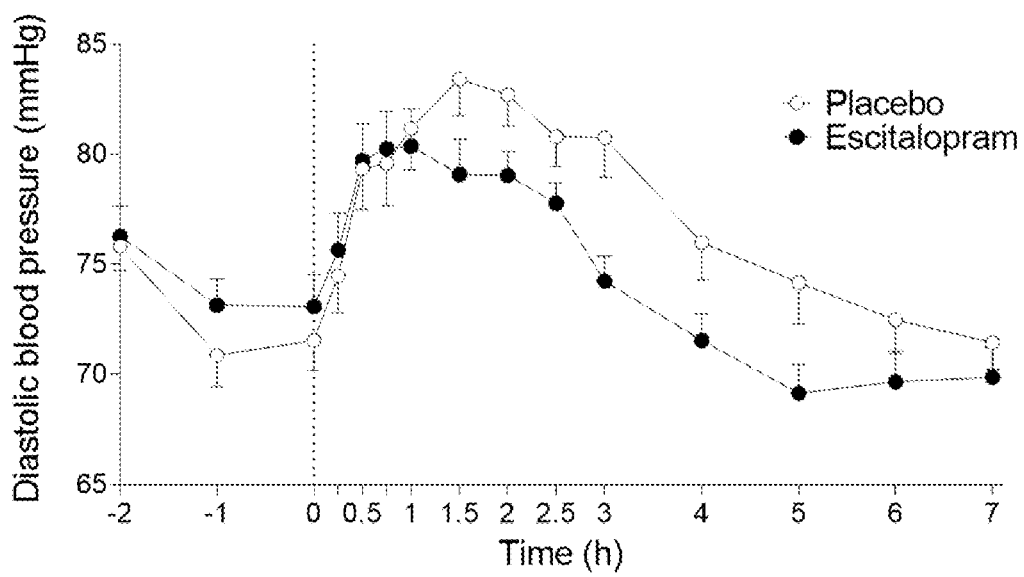
Figure 21A:
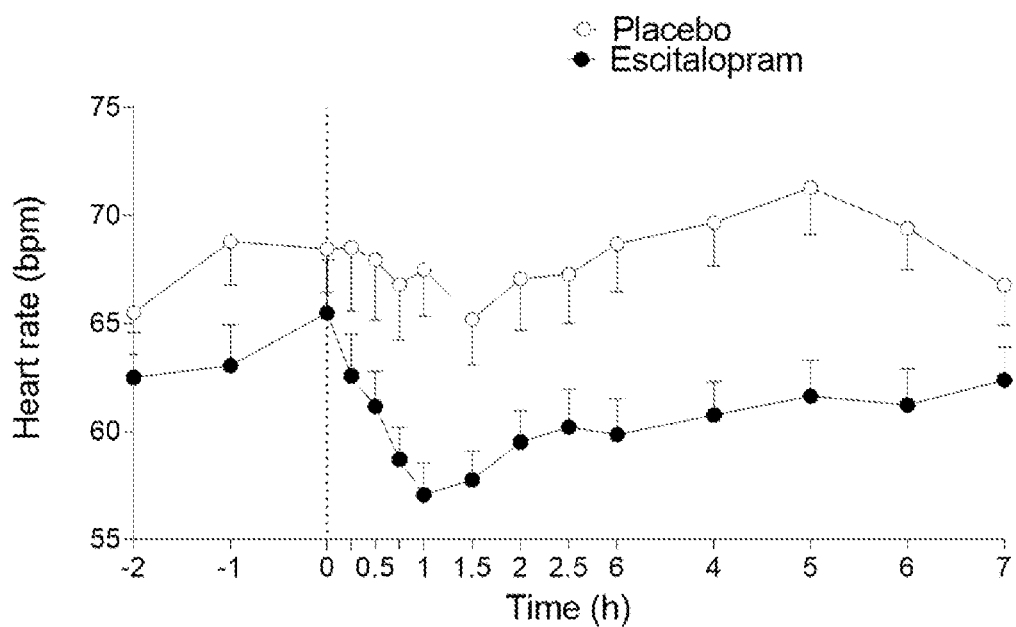
FIG. 21A is a graph showing effects of psilocybin on heart rate and FIG. 21B is a graph showing effects of psilocybin on body temperature after escitalopram and placebo.
Figure 21B:
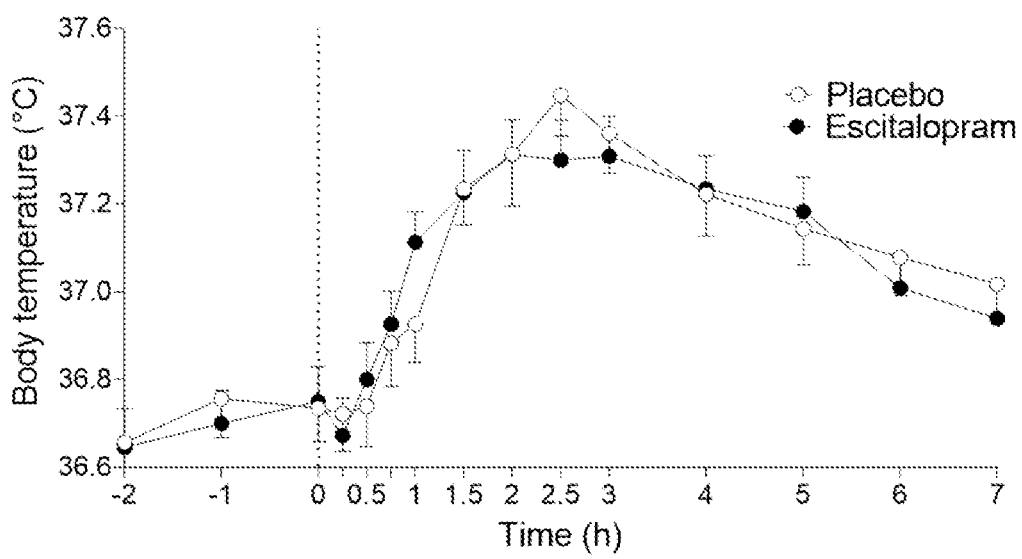

Psilocybin produced marked subjective effects on the VAS (FIGS. 3-13) and AMRS (FIGS. 14-16) and robust alterations of mind in the 5D-ASC (FIGS. 17-18), MEQ30 (FIG. 19), and MEQ43 (FIG. 19). Psilocybin mainly induced good drug effects (FIG. 3B) and only moderate bad drug effects (FIG. 6A) and anxiety (FIG. 6B). Psilocybin also moderately increased systolic and diastolic blood pressure (FIGS. 20A and 20B, respectively), body temperature (FIG. 21B), and rate-pressure product (FIG. 22), and pupil size (FIGS. 23A and 23B), while heart rate changed only minimally (FIG. 21A).

Figure 16:
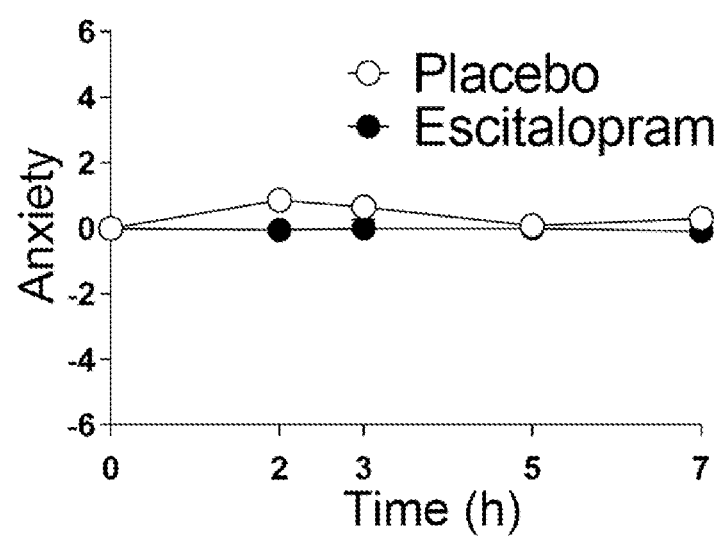
FIG. 16 is a graph showing anxiety induced by psilocybin after escitalopram and placebo pretreatment.

Overall, escitalopram pretreatment had only a small effect on the response to psilocybin compared to placebo pretreatment. Escitalopram slightly, but significantly reduced any drug effects in response to psilocybin (P=0.015 vs. Placebo). Escitalopram did not significantly reduce good drug effects of psilocybin but it markedly and significantly reduced by 50% peak bad drug effects (P=0.004 vs. Placebo) and peak anxiety (P=0.004 vs. Placebo) induced by psilocybin (FIG. 24). Consistently, escitalopram also significantly reduced psilocybin-induced anxiety in the AMRS (P=0.007; FIG. 16 and FIG. 25), anxious ego dissolution and anxiety in the 5D-ASC (P=0.029 and 0.026, respectively; FIGS. 17, 18, and 26) and nadir effects in the MEQ43 (P=0.001; FIGS. 19 and 27).

Figure 22:
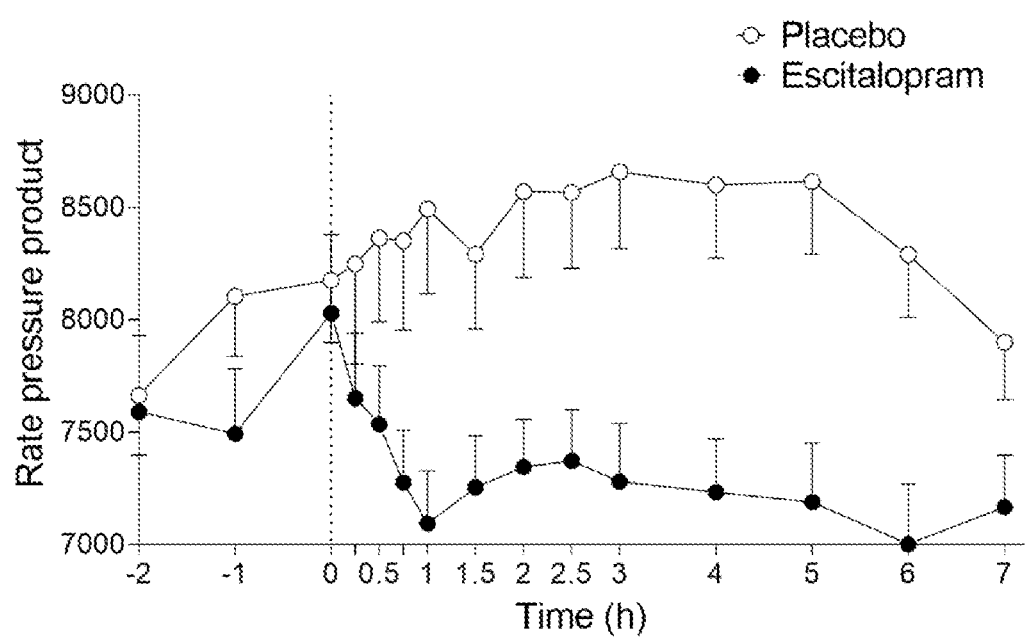
FIG. 22 is a graph showing effects of psilocybin on rate pressure product after escitalopram and placebo pretreatment.
Figure 23A:
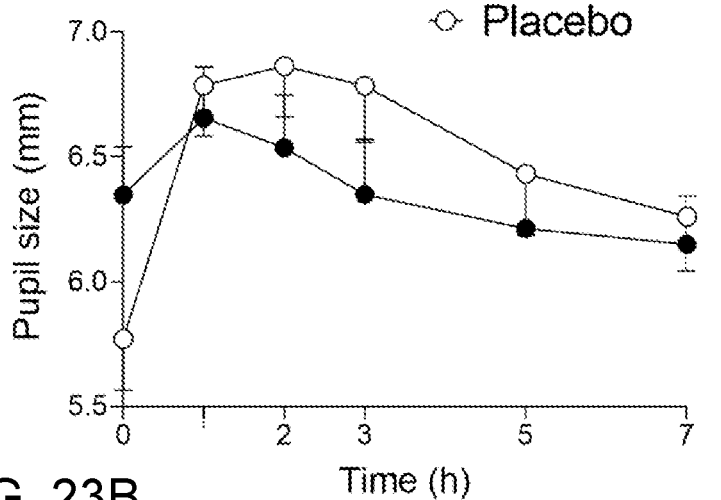
FIG. 23A is a graph showing effects of psilocybin pupil size.
Figure 23B:
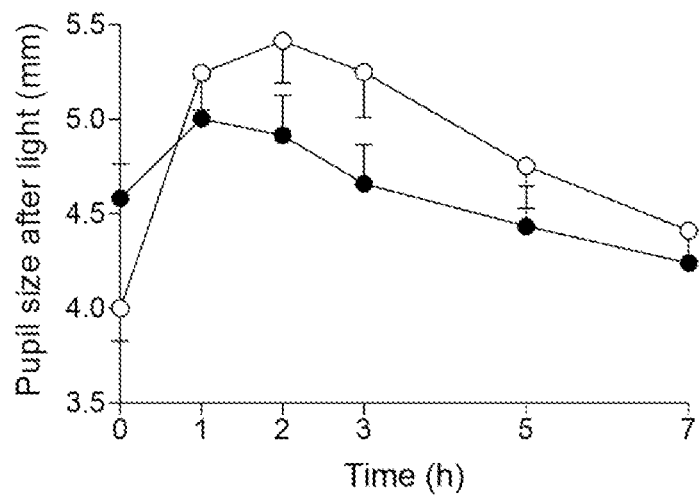
FIG. 23B is a graph showing effects on pupil size after light.
Figure 23C:
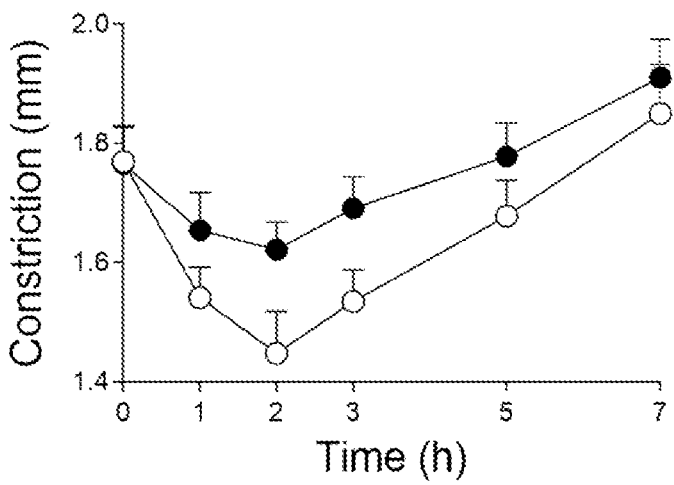
FIG. 23C is a graph showing effects on pupil constriction after escitalopram and placebo.

Escitalopram also influenced the autonomic response to psilocybin. Specifically, escitalopram reduced psilocybin-induced elevations in peak systolic blood pressure (P<0.001; FIGS. 20A and 28), peak diastolic blood pressure (P=0.017; FIGS. 20B and 28), rate pressure product (P=0.001; FIGS. 22 and 28), and pupil dilation (P=0.002; FIGS. 23A, 23B and 28).

Escitalpram also reduced acute adverse effects associated with psilocybin compared with placebo (P=0.028; FIG. 28).

Psilocin, the active metabolite of psilocybin, was metabolized to inactive 4-HIAA and psilocin-glucuronide (FIG. 29). The maximal plasma concentration of non-glucuronidated free and psychoactive active psilocin was reached after a mean time of 2 hours (FIG. 29). The elimination half-life of the non-glucuronidated psilocin was 2 hours (FIG. 29). This half-life is consistent with the short duration of action of psilocin consistent with the view that the non-glucuronidated psilocin is responsible for the psychoactive effects. Glucuronidated psilocin peak concentrations were reached after a mean time of approximately 3.2-3.4 hours after administration and the elimination half-life was 4.1 and 4.5 hours after placebo and escitalopram, respectively (FIG. 29). Escitalopram did not relevantly or significantly alter the pharmacokinetics of psilocin (FIG. 29).

Figures 30A, 30B:
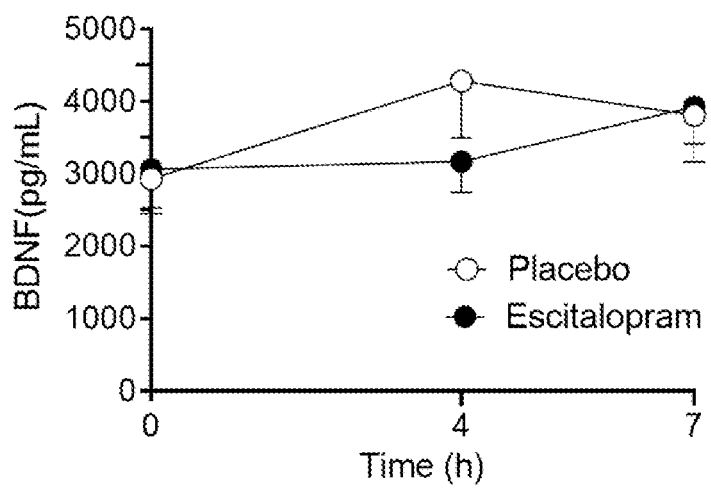
FIG. 30A is a graph and FIG. 30B a table representing the effects of psilocybin on brain derived neurotrophic factor (BDNF) plasma concentrations.

Psilocybin slightly increased BDNF plasma levels at 4 h after placebo and at 7 hours after escitalopram or placebo (FIGS. 30A and 30B). Escitalopram did not significantly alter the psilocybin-induced moderate increase in BDNF (FIGS. 30A and 30B).

Taken together, escitalopram pretreatment had no relevant effect on the positive mood effects of psilocybin but significantly reduced bad drug effects, anxiety, adverse autonomic and other adverse effects of psilocybin compared with placebo pretreatment.

Escitalopram plasma concentrations were (mean, range) 41 (35-53) ng/mL which is in the upper range of concentrations considered therapeutic in patients (Florio et al., 2017).

Escitalopram also reduced acute adverse effects assessed on the LC and associated with psilocybin compared with placebo (P=0.028; FIG. 28). There were additional adverse events reported after psilocybin administration in the evening of the treatment day of day after treatment. These adverse aftereffects after psilocybin administration included headaches (six subjects after escitalopram and six after placebo), flash backs (one subject after escitalopram and one after placebo), nausea (one subject after escitalopram and one after placebo), abdominal bloating (one subjects after escitalopram) and vasovagal syncope (one subject after placebo) and lack of energy (one subjects after escitalopram). Taken together, the type and amount of adverse events following psilocybin administration was comparable after escitalopram and placebo pretreatment.

Psilocybin did not increase $QT_c$ times at 2.5 hours after administration compared with times measured 1 hour before administration (FIG. 28). Escitalopram did not alter $QT_c$ time before or after psilocybin administration compared with placebo (FIG. 28).

Figure 31A:
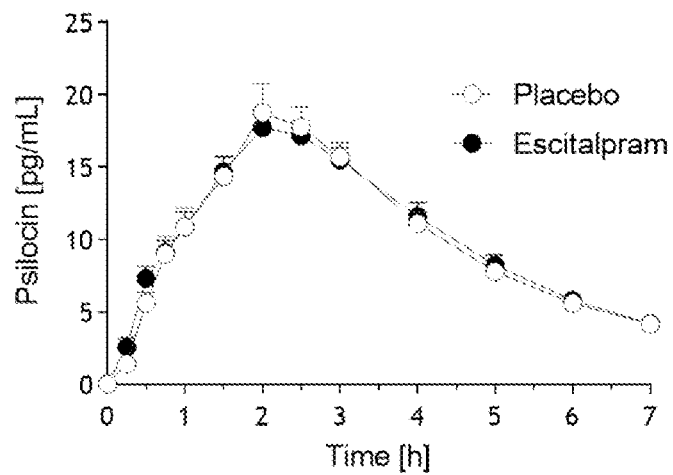
FIG. 31A is a graph showing plasma concentrations of psilocin and FIG. 31B is a graph showing plasma concentrations of psilocin glucuronide after administration of psilocybin and after escitalopram and placebo pretreatment.
Figure 31B:
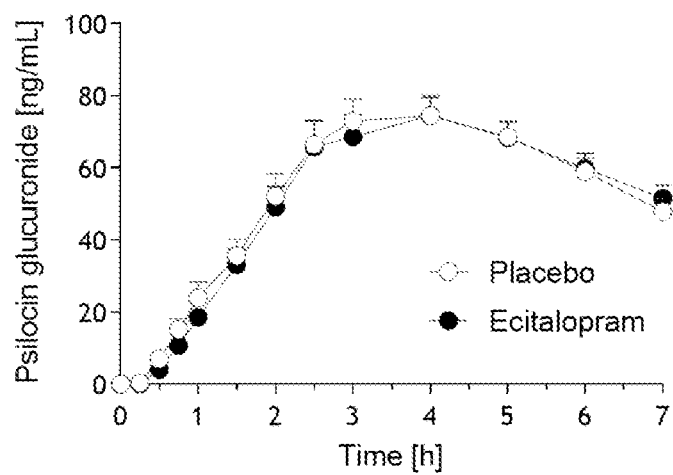
Figure 32A:
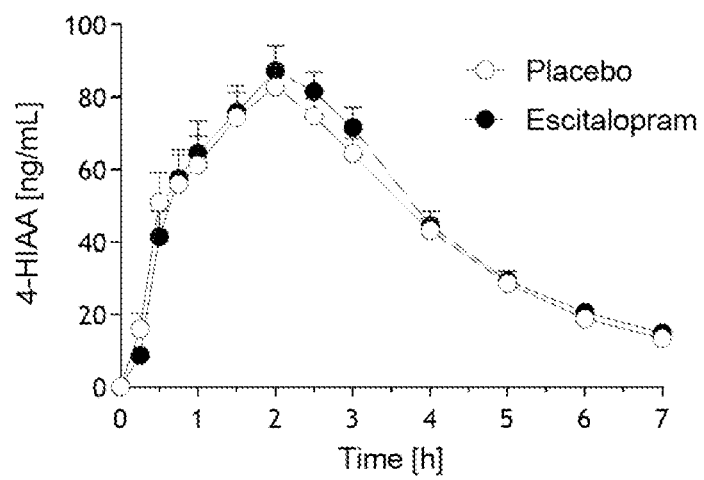
FIG. 32A is a graph showing plasma concentrations of 4-HIAA after administration of psilocybin and after escitalopram and placebo pretreatment and FIG. 32B is a graph showing plasma concentrations of escitalopram after administration of psilocybin and after escitalopram pretreatment.
Figure 32B:
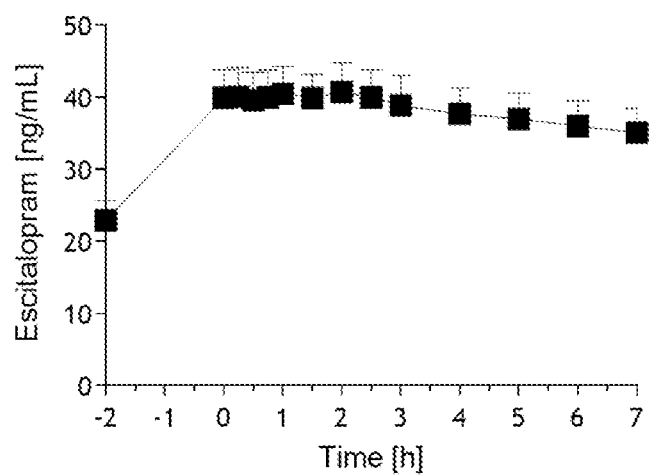
Figure 33:
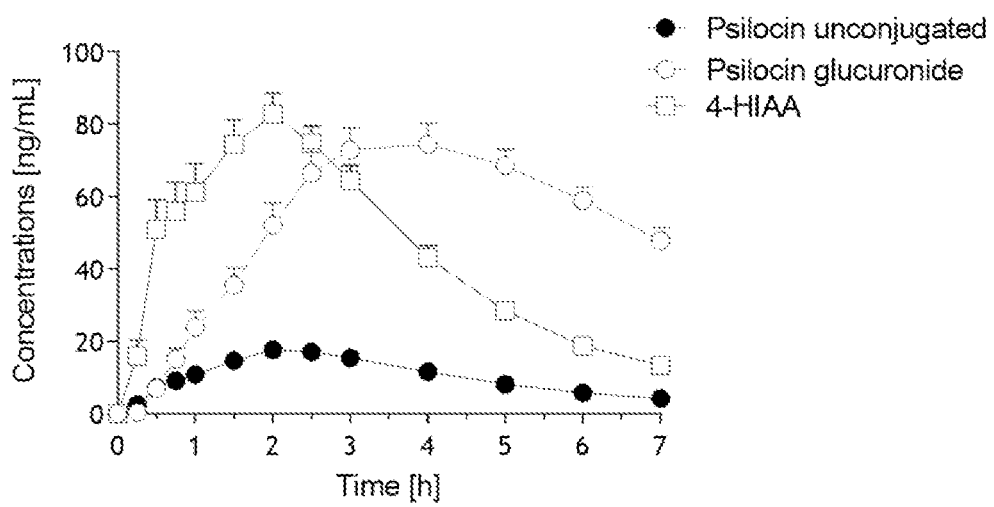
FIG. 33 is a graph showing plasma concentrations of 4-HIAA, unconjugated psilocin, and psilocin glucuronide.

Plasma concentrations of psilocin and 4-HIAA were quantified before- and up to seven hours post-treatment. All samples were reanalyzed after deglucuronidation. The plasma levels of psilocin glucuronide were determined using the difference between samples that were incubated with and without glucuronidase corresponding to the total amount of conjugated metabolites. A large proportion of psilocin underwent glucuronidation, whereas 4-HIAA was not conjugated. 4-HIAA concentrations were similar when analyzed before or after deglucuronidation (FIG. 29). Psilocin, the active metabolite of psilocybin, was metabolized to approximately similar extents to inactive 4-HIAA and psilocinglucuronide (FIG. 29, FIG. 32A, FIG. 32B, FIG. 31B, FIG. 33). The increase in metabolite concentrations over time is faster for 4-HIAA compared to the glucuronide (FIG. 33). The maximal plasma concentration of the nonconjugated and psychoactive active psilocin was reached after a mean time of 2 hours (FIG. 29, FIG. 31A). The elimination half-life of the nonconjugated psilocin was 2 hours (FIG. 29, FIG. 31A). This half-life and the time course of the plasma concentrations of the nonconjugated psilocin (FIG. 31A, FIG. 33) are consistent with the short duration of action of psilocin (FIG. 3A) and consistent with the view that the nonconjugated psilocin is responsible for the psychoactive effects of psilocybin and that the glucuronide is not psychoactive. Peak concentrations of psilocin glucuronide were reached after a mean time of 3.8 and 3.74 hours after administration and the elimination half-life was 4.5 and 5.2 hours after placebo and escitalopram, respectively (FIG. 29, FIG. 31B). Escitalopram did not relevantly or significantly alter the pharmacokinetics of psilocin (FIGURE 29, FIG. 31A), psilocin glucuronide (FIG. 29, FIG. 31B), and 4-HIAA (FIG. 29, FIG. 32A).

Psilocybin slightly increased BDNF plasma levels at 4 hours after placebo and at 7 hours after escitalopram or placebo (FIGS. 30A and 30B). Escitalopram did not significantly alter the psilocybin-induced moderate increase in BDNF (FIGS. 30A and 30B).

Taken together, escitalopram pretreatment had no relevant effect on the positive mood effects of psilocybin but significantly reduced bad drug effects, anxiety, adverse autonomic and other adverse effects of psilocybin compared with placebo pretreatment.

Figure 3A:
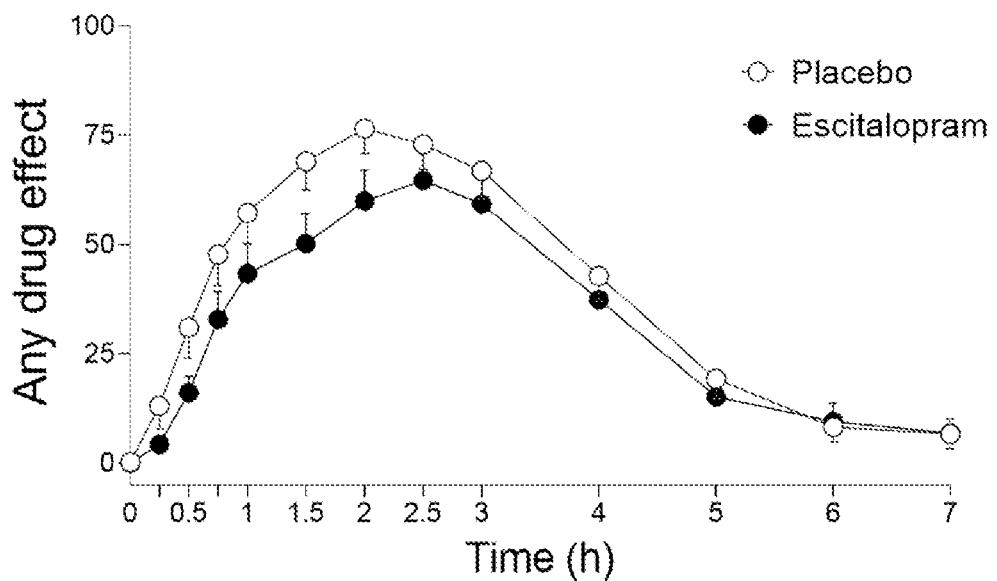
FIG. 3A is a graph showing acute any drug effect and FIG. 3B is a graph showing good drug effects of psilocybin after escitalopram and placebo pretreatment.
Figure 3B:
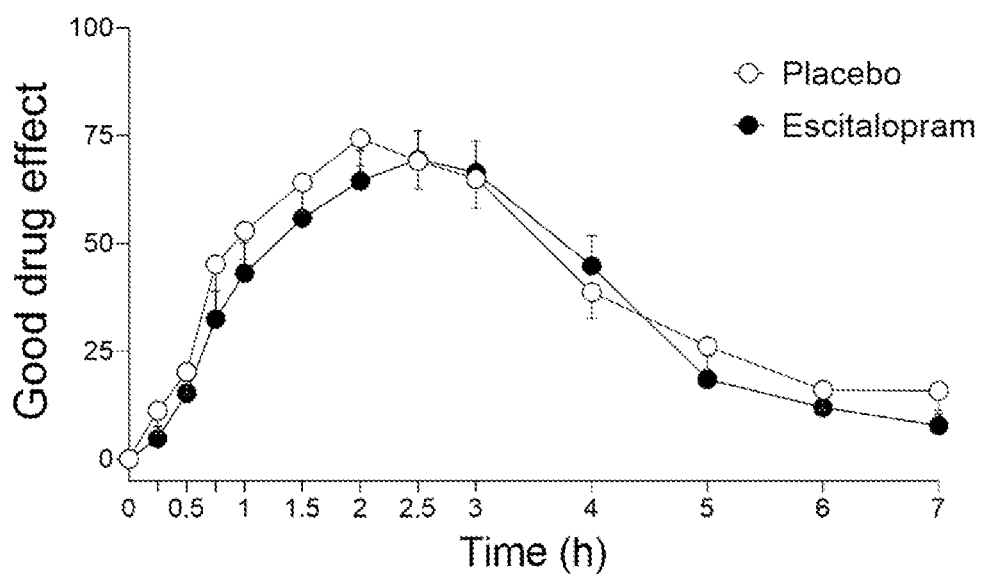
Figure 4A:
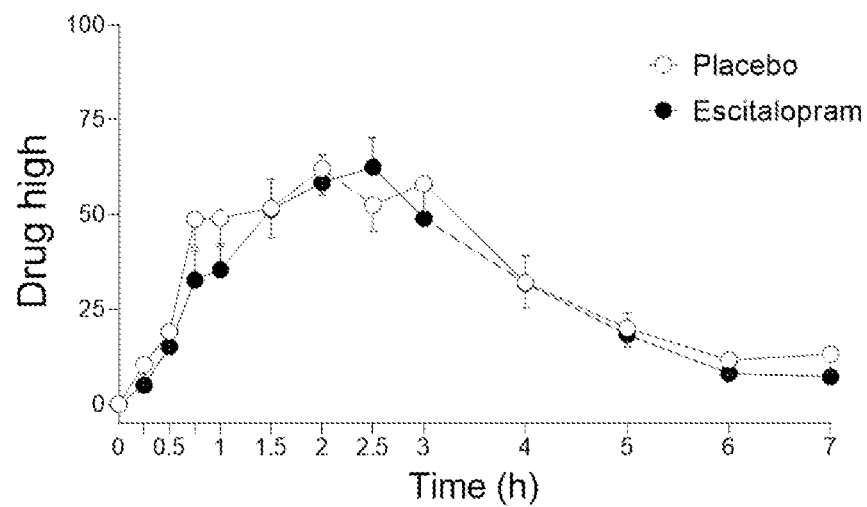
FIG. 4A is a graph showing acute drug high and FIG. 4B is a graph showing feeling stimulated induced by psilocybin after escitalopram and placebo pretreatment.
Figure 4B:
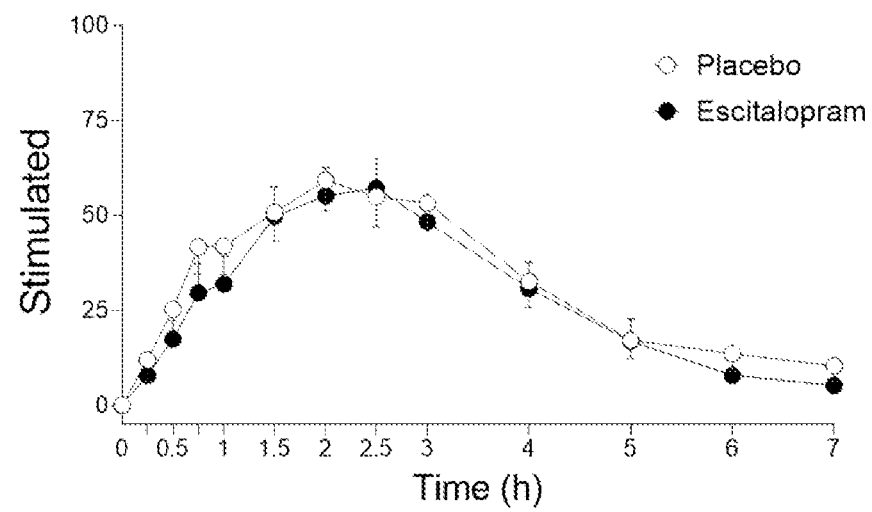
Figure 5A:
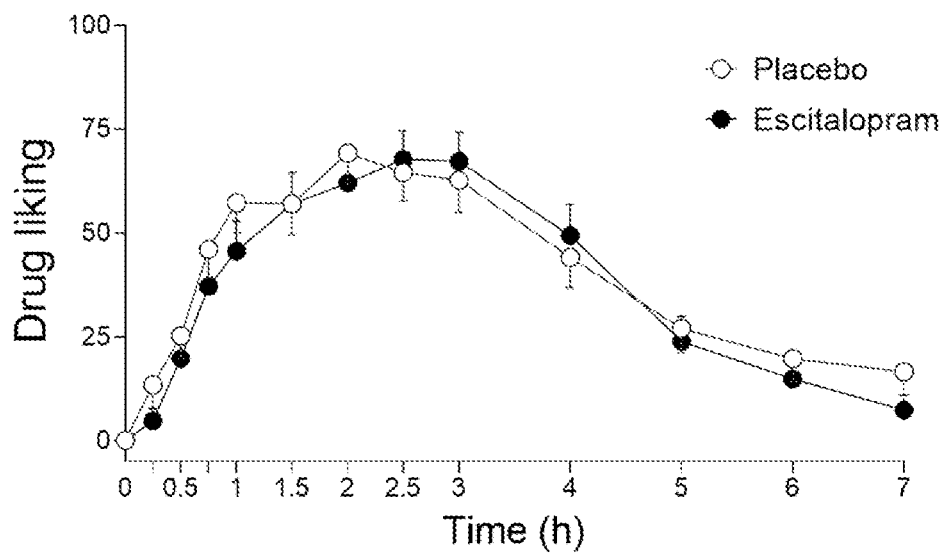
FIG. 5A is a graph showing drug liking and FIG. 5B is a graph showing feeling happy induced by psilocybin after escitalopram and placebo pretreatment.
Figure 5B:
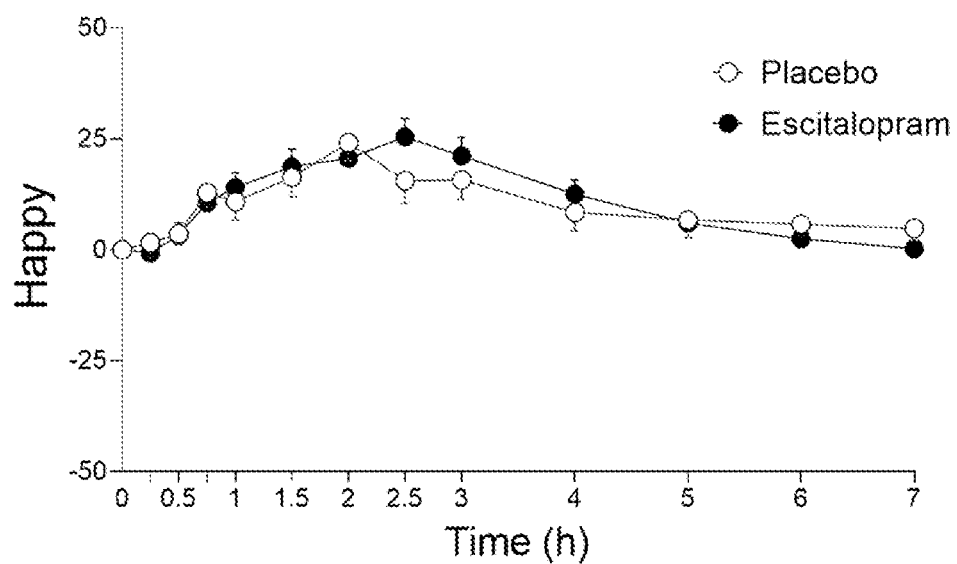

Escitalopram peak plasma concentrations were (mean, range) 41 (35-53) ng/mL (FIG. 29, FIG. 32B) which is in the upper range of concentrations considered therapeutic in patients (Florio et al., 2017). Additionally, concentrations were high (<35 ng/mL) in all subjects and remained elevated throughout the time of the psilocybin effect (FIG. 32B, FIG. 3A). Thus, escitalopram concentrations similar in the present healthy subjects to those in patients on long-term treatment and creating a state in the healthy subjects similar to that in patients on antidepressant treatment. There was one severe adverse event in the example study. A participant who started on the escitalopram pretreatment had a symptomatic vertebral disc hernia which was operated, and the patient dropped out of the study after five days of pretreatment and prior to psilocybin administration.

The pretreatment also resulted in a series of adverse events. Adverse events any time during escitalopram pretreatment included nausea (eight subjects), headache (6), tiredness (6), decreased libido (5), feeling depressed (3), loss of appetite (3), diarrhea (2), restless legs (2), increased appetite (2), bruxism (2), insomnia (2), dysorgasmia (2), dizziness (2), difficulty concentrating (1), difficulty concentrating (1), visual disturbance (1). Adverse events during placebo pretreatment included nausea (three subjects), tiredness (3), nightmares (3), headaches (2), insomnia (2), diarrhea (1), feeling depressed (1), bruxism (1), and difficulty concentrating (1).

Escitalopram did not alter the expression of the HRT2A or SLC6A4 genes or of any of the reference genes measured at the end of the two-week pretreatment period and compared with placebo pretreatment.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Akimoto H, Oshima S, Sugiyama T, Negishi A, Nemoto T, & Kobayashi D (2019). Changes in brain metabolites related to stress resilience: metabolomic analysis of the hippocampus in a rat model of depression. Behav Brain Res 359: 342-352.
2. Andersson M, Persson M, & Kjellgren A (2017). Psychoactive substances as a last resort—a qualitative study of self-treatment of migraine and cluster headaches. Harm Reduct J 14: 60.
3. Barrett F S, Johnson M W, & Griffiths R R (2015). Validation of the revised Mystical Experience Questionnaire in experimental sessions with psilocybin. J Psychopharmacol 29: 1182-1190.
4. Becker A M, Holze F, Grandinetti T, Klaiber A, Toedtli V E, Kolaczynska K E, Duthaler U, Varghese N, Eckert A, Grunblatt E, & Liechti M E (2021). Acute effects of psilocybin after escitalopram or placebo pretreatment in a randomized, double-blind, placebo-controlled, cross-over study in healthy subjects. Clin Pharmacol Ther: doi: 10.1002/cpt.2487.
5. Black K, Shea C, Dursun S, & Kutcher S (2000). Selective serotonin reuptake inhibitor discontinuation syndrome: proposed diagnostic criteria. J Psychiatry Neurosci 25: 255-261.
6. Bogenschutz M P (2013). Studying the effects of classic hallucinogens in the treatment of alcoholism: rationale, methodology, and current research with psilocybin. Curr Drug Abuse Rev 6: 17-29.
7. Bogenschutz M P, Forcehimes A A, Pommy J A, Wilcox C E, Barbosa P C, & Strassman R J (2015). Psilocybinassisted treatment for alcohol dependence: a proof-of-concept study. J Psychopharmacol 29: 289-299.
8. Bonson K R, Buckholtz J W, & Murphy D L (1996). Chronic administration of serotnergic antidepressants attenuates the subjective effects of LSD in humans. Neuropsychopharmacology 14: 425-436.
9. Bonson K R, & Murphy D L (1996). Alterations in response to LSD in humans associated with chronic administration of tricyclic antidepressants, monoamine oxidase inhibitors or lithium. Behav Brain Res 73: 229-233.
10. Carhart-Harris R, Giribaldi B, Watts R, Baker-Jones M, Murphy-Beiner A, Murphy R, Martell J, Blemings A, Erritzoe D, & Nutt D J (2021). Trial of psilocybin versus escitalopram for depression. N Engl J Med 384: 1402-1411.
11. Carhart-Harris R L, Bolstridge M, Day C M J, Rucker J, Watts R, Erritzoe D E, Kaelen M, Giribaldi B, Bloomfield M, Pilling S, Rickard J A, Forbes B, Feilding A, Taylor D, Curran H V, & Nutt D J (2018). Psilocybin with psychological support for treatment-resistant depression: six-month follow-up. Psychopharmacology (Berl) 235: 399-408.
12. Carhart-Harris R L, Bolstridge M, Rucker J, Day C M, Erritzoe D, Kaelen M, Bloomfield M, Rickard J A, Forbes B, Feilding A, Taylor D, Pilling S, Curran V H, & Nutt D J (2016). Psilocybin with psychological support for treatment-resistant depression: an open-label feasibility study. Lancet Psychiatry 3: 619-627.
13. Carhart-Harris R L, & Goodwin G M (2017). The therapeutic potential of psychedelic drugs: past, present, and future. Neuropsychopharmacology 42: 2105-2113.
14. Davis A K, Barrett F S, May D G, Cosimano M P, Sepeda N D, Johnson M W, Finan P H, & Griffiths R R (2021). Effects of psilocybin-assisted therapy on major depressive disorder: a randomized clinical trial. JAMA Psychiatry 78: 481-489.
15. de Almeida R N, Galvao A C M, da Silva F S, Silva E, Palhano-Fontes F, Maia-de-Oliveira J P, de Araujo L B, Lobao-Soares B, & Galvao-Coelho N L (2019). Modulation of serum brain-derived neurotrophic factor by a single dose of ayahuasca: observation from a randomized controlled trial. Front Psychol 10: 1234.
16. de Montigny C, Chaput Y, & Blier P (1990). Modification of serotonergic neuron properties by long-term treatment with serotonin reuptake blockers. J Clin Psychiatry 51 Suppl B: 4-8.
17. DeMaar E W J, Williams H L, Miller A I, & Pfeiffer C C (1960). Effects in man of single and combined oral doses of reserpine, iproniazid, and D-lysergic acid diethylamide. Clin Pharmacol Ther 1: 23-30.
18. Dittrich A (1998). The standardized psychometric assessment of altered states of consciousness (ASCs) in humans. Pharmacopsychiatry 31 (Suppl 2): 80-84.
19. Dominguez-Clave E, Soler J, Elices M, Pascual J C, Alvarez E, de la Fuente Revenga M, Friedlander P, Feilding A, & Riba J (2016). Ayahuasca: Pharmacology, neuroscience and therapeutic potential. Brain Res Bull 126: 89-101.
20. Dong C, Ly C, Dunlap L E, Vargas M V, Sun J, Hwang I W, Azinfar A, Oh W C, Wetsel W C, Olson D E, & Tian L (2021). Psychedelic-inspired drug discovery using an engineered biosensor. Cell 184: 2779-2792.e2718.
21. Dos Santos R G, Osorio F L, Crippa J A, Riba J, Zuardi A W, & Hallak J E (2016). Antidepressive, anxiolytic, and antiaddictive effects of ayahuasca, psilocybin and lysergic acid diethylamide (LSD): a systematic review of clinical trials published in the last 25 years. Ther Adv Psychopharmacol 6: 193-213.
22. FDA (2017). Lexapro (Escitalopram) drug label (Reference ID: 4036381). In FDA.
23. Florio V, Porcelli S, Saria A, Serretti A, & Conca A (2017). Escitalopram plasma levels and antidepressant response. Eur Neuropsychopharmacol 27: 940-944.
24. Garcia-Romeu A, Davis A K, Erowid F, Erowid E, Griffiths R R, & Johnson M W (2019). Cessation and reduction in alcohol consumption and misuse after psychedelic use. J Psychopharmacol: 269881119845793.
25. Garcia-Romeu A, Griffiths R R, & Johnson M W (2014). Psilocybin-occasioned mystical experiences in the treatment of tobacco addiction. Curr Drug Abuse Rev 7: 157-164.
26. Gasser P, Holstein D, Michel Y, Doblin R, Yazar-Klosinski B, Passie T, & Brenneisen R (2014). Safety and efficacy of lysergic acid diethylamide-assisted psychotherapy for anxiety associated with life-threatening diseases. J Nerv Ment Dis 202: 513-520.
27. Gasser P, Kirchner K, & Passie T (2015). LSD-assisted psychotherapy for anxiety associated with a life-threatening disease: a qualitative study of acute and sustained subjective effects. J Psychopharmacol 29: 57-68.
28. Gillman P K (2010). Triptans, serotonin agonists, and serotonin syndrome (serotonin toxicity): a review. Headache 50: 264-272.
29. Griffiths R, Richards W, Johnson M, McCann U, & Jesse R (2008). Mystical-type experiences occasioned by psilocybin mediate the attribution of personal meaning and spiritual significance 14 months later. J Psychopharmacol 22: 621-632.
30. Griffiths R R, Johnson M W, Carducci M A, Umbricht A, Richards W A, Richards B D, Cosimano M P, & Klinedinst M A (2016). Psilocybin produces substantial and sustained decreases in depression and anxiety in patients with life-threatening cancer: a randomized double-blind trial. J Psychopharmacol 30: 1181-1197.
31. Griffiths R R, Richards W A, McCann U, & Jesse R (2006). Psilocybin can occasion mystical-type experiences having substantial and sustained personal meaning and spiritual significance. Psychopharmacology (Berl) 187: 268-283; discussion 284-292.
32. Grob C S, Danforth A L, Chopra G S, Hagerty M, McKay C R, Halberstadt A L, & Greer G R (2011). Pilot study of psilocybin treatment for anxiety in patients with advanced-stage cancer. Arch Gen Psychiatry 68: 71-78.
33. Grof S, & Dytrych Z (1965). Blocking of LSD reaction by premedication with Niamid. Act Nerv Super (Praha) 7: 306.
34. Grunblatt E, Bartl J, Zehetmayer S, Ringel T M, Bauer P, Riederer P, & Jacob C P (2009). Gene expression as peripheral biomarkers for sporadic Alzheimer's disease. J Alzheimers Dis 16: 627-634.
35. Haile C N, Murrough J W, Iosifescu D V, Chang L C, Al Jurdi R K, Foulkes A, Iqbal S, Mahoney J J, 3rd, De La Garza R, 2nd, Charney D S, Newton T F, & Mathew S J (2014). Plasma brain derived neurotrophic factor (BDNF) and response to ketamine in treatment-resistant depression. Int J Neuropsychopharmacol 17: 331-336.
36. Hasler F, Bourquin D, Brenneisen R, Bar T, & Vollenweider F X (1997). Determination of psilocin and 4-hydroxyindole-3-acetic acid in plasma by HPLC-ECD and pharmacokinetic profiles of oral and intravenous psilocybin in man. Pharm Acta Helv 72: 175-184.
37. Hintzen A, & Passie T (2010) The pharmacology of LSD: a critical review. Oxford University Press: Oxford.
38. Holze F, Duthaler U, Vizeli P, Muller F, Borgwardt S, & Liechti M E (2019). Pharmacokinetics and subjective effects of a novel oral LSD formulation in healthy subjects. Br J Clin Pharmacol 85: 1474-1483.
39. Holze F, Vizeli P, Ley L, Muller F, Dolder P, Stocker M, Duthaler U, Varghese N, Eckert A, Borgwardt S, & Liechti M E (2021). Acute dose-dependent effects of lysergic acid diethylamide in a double-blind placebo-controlled study in healthy subjects. Neuropsychopharmacology 46: 537-544.

40. Hutten N, Mason N L, Dolder P, Theunissen E L, Holze F, Liechti M E, Varghese N, Eckert A, Feilding A, Ramaekers J G, & Kuypers K P (2020). Low doses of LSD acutely increases BDNF blood plasma levels in healthy volunteers. ACS Pharmacol Transl Sci 4: 461-466.
41. Hysek C M, Vollenweider F X, & Liechti M E (2010). Effects of a b-blocker on the cardiovascular response to MDMA (ecstasy). Emerg Med J 27: 586-589.
42. Janke W, & Debus G (1978) Die Eigenschaftswörterliste. Hogrefe: Göttingen.
43. Johnson M W, Garcia-Romeu A, Cosimano M P, & Griffiths R R (2014). Pilot study of the 5-HT$_2$A R agonist psilocybin in the treatment of tobacco addiction. J Psychopharmacol 28: 983-992.
44. Johnson M W, Garcia-Romeu A, & Griffiths R R (2016). Long-term follow-up of psilocybin-facilitated smoking cessation. Am J Drug Alcohol Abuse 43: 55-60.
45. Koenig A M, & Thase M E (2009). First-line pharmacotherapies for depression—what is the best choice? Pol Arch Med Wewn 119: 478-486.
46. Kolaczynska K E, Liechti M E, & Duthaler U (2021). Development and validation of an LC-MS/MS method for the bioanalysis of psilocybin's main metabolites, psilocin and 4-hydroxyindole-3-acetic acid, in human plasma. J Chromatogr B Analyt Technol Biomed Life Sci 1164: 122486.
47. Krebs T S, & Johansen P O (2012). Lysergic acid diethylamide (LSD) for alcoholism: meta-analysis of randomized controlled trials. J Psychopharmacol 26: 994-1002.
48. Liechti M E (2017). Modern clinical research on LSD. Neuropsychopharmacology 42: 2114-2127.
49. Liechti M E, Dolder P C, & Schmid Y (2017). Alterations in conciousness and mystical-type experiences after acute LSD in humans. Psychopharmacology 234: 1499-1510.
50. Ly C, Greb A C, Cameron L P, Wong J M, Barragan E V, Wilson P C, Burbach K F, Soltanzadeh Zarandi S, Sood A, Paddy M R, Duim W C, Dennis M Y, McAllister A K, Ori-McKenney K M, Gray J A, & Olson D E (2018). Psychedelics promote structural and functional neural plasticity. Cell Rep 23: 3170-3182.
51. Madsen M K, Fisher P M, Burmester D, Dyssegaard A, Stenbaek D S, Kristiansen S, Johansen S S, Lehel S, Linnet K, Svarer C, Erritzoe D, Ozenne B, & Knudsen G M (2019). Psychedelic effects of psilocybin correlate with serotonin 2A receptor occupancy and plasma psilocin levels. Neuropsychopharmacology 44: 1328-1334.
52. Maracek P, Bakalar E, & Zeman K (1968). Attempt of blocking LSD intoxication with tranylcypromine. Act Nery 10: 276-277.
53. Nichols D E (2016). Psychedelics. Pharmacol Rev 68: 264-355.
54. Nichols D E, Johnson M W, & Nichols C D (2017). Psychedelics as medicines: an emerging new paradigm. Clin Pharmacol Ther 101: 209-219.
55. Palhano-Fontes F, Barreto D, Onias H, Andrade K C, Novaes M M, Pessoa J A, Mota-Rolim S A, Osorio F L, Sanches R, Dos Santos R G, Tofoli L F, de Oliveira Silveira G, Yonamine M, Riba J, Santos F R, Silva-Junior A A, Alchieri J C, Galvao-Coelho N L, Lobao-Soares B, Hallak J E C, Arcoverde E, Maia-de-Oliveira J P, & Araujo D B (2019). Rapid antidepressant effects of the psychedelic ayahuasca in treatment-resistant depression: a randomized placebo-controlled trial. Psychol Med 49: 655-663.
56. Passie T, & Halpern J H (2014). The pharmacology of hallucinogens. In The ASAM principles of addiction medicine. ed Ries R., K. Wolters Kluver: Alphen aan de Rijn, The Netherlands, pp 235-255.
57. Passie T, Halpern J H, Stichtenoth D O, Emrich H M, & Hintzen A (2008). The pharmacology of lysergic acid diethylamide: a review. CNS Neurosci Ther 14: 295-314.
58. Passie T, Seifert J, Schneider U, & Emrich H M (2002). The pharmacology of psilocybin. Addict Biol 7: 357-364.
59. Pratt Laura A. B D J, Gu Qiuping (2017). Antidepressant Use Among Persons Aged 12 and Over: United States, 2011-2014. In NCHS data brief Hyattsville, MD: National Center for Health Statistics.
60. Preller K H, Herdener M, Pokorny T, Planzer A, Kraehenmann R, Stämpfli P, Liechti M E, Seifritz E, & Vollenweider F X (2017). The fabric of meaning and subjective effects in LSD-induced states depend on serotonin 2A receptor activation Curr Biol 27: 451-457.
61. Rickli A, Moning O D, Hoener M C, & Liechti M E (2016). Receptor interaction profiles of novel psychoactive tryptamines compared with classic hallucinogens. Eur Neuropsychopharmacol 26: 1327-1337.
62. Roseman L, Nutt D J, & Carhart-Harris R L (2017). Quality of acute psychedelic experience predicts therapeutic efficacy of psilocybin for treatment-resistant depression. Front Pharmacol 8: 974.
63. Ross S, Bossis A, Guss J, Agin-Liebes G, Malone T, Cohen B, Mennenga S E, Belser A, Kalliontzi K, Babb J, Su Z, Corby P, & Schmidt B L (2016). Rapid and sustained symptom reduction following psilocybin treatment for anxiety and depression in patients with life-threatening cancer: a randomized controlled trial. J Psychopharmacol 30: 1165-1180.
64. Rucker J J H, Iliff J, & Nutt D J (2018). Psychiatry & the psychedelic drugs. Past, present & future. Neuropharmacology 142: 200-218.
65. Sanches R F, de Lima Osorio F, Dos Santos R G, Macedo L R, Maia-de-Oliveira J P, Wichert-Ana L, de Araujo D B, Riba J, Crippa J A, & Hallak J E (2016). Antidepressant Effects of a Single Dose of Ayahuasca in Patients With Recurrent Depression: A SPECT Study. J Clin Psychopharmacol 36: 77-81.
66. Schmid Y, Gasser P, Oehen P, & Liechti M E (2021). Acute subjective effects in LSD- and MDMA-assisted psychotherapy. J Psychopharmacol 35: 362-374.
67. Schmid Y, & Liechti M E (2018). Long-lasting subjective effects of LSD in normal subjects. Psychopharmacology (Berl) 235: 535-545.
68. Strassman R J (1992). Human halluciongen interactions with drugs affecting serotonergic neurotransmission. Neuropsychopharmacology 7: 241-243.
69. Studerus E, Gamma A, & Vollenweider F X (2010). Psychometric evaluation of the altered states of consciousness rating scale (OAV). PLoS One 5: e12412.
70. Swissmedic (2020). Arzneimittelinformation Schweizerisches Heilmittelinstitut: Bern.
71. Tamam L, & Ozpoyraz N (2002). Selective serotonin reuptake inhibitor discontinuation syndrome: a review. Adv Ther 19: 17-26.
72. Vollenweider F X, & Preller K H (2020). Psychedelic drugs: neurobiology and potential for treatment of psychiatric disorders. Nat Rev Neurosci 21: 611-624.
73. Vollenweider F X, Vollenweider-Scherpenhuyzen M F, Babler A, Vogel H, & Hell D (1998). Psilocybin induces schizophrenia-like psychosis in humans via a serotonin-2 agonist action. Neuroreport 9: 3897-3902.

74. Wittchen H U, Wunderlich U, Gruschwitz S, & Zaudig M (1997) SKID-I: Strukturiertes Klinisches Interview für DSM-IV. Hogrefe-Verlag: Göttingen.
75. Yang T, Nie Z, Shu H, Kuang Y, Chen X, Cheng J, Yu S, & Liu H (2020). The role of BDNF on neural plasticity in depression. Front Cell Neurosci 14: 82-82.
76. Zerssen D V (1976) Die Beschwerden-Liste. Münchener Informationssystem. Psychis: München.

What is claimed is:

1. A method of enhancing positive effects of a psychedelic, including the steps of:
pretreating an individual with an antidepressant;
administering a psychedelic to the individual; and
inducing a more positive psychological state in the individual with the antidepressant-psychedelic combination compared with the psychedelic alone, wherein the antidepressant is escitalopram administered at a dose of 10-20 mg and the psychedelic is psilocybin and is administered at dose of 10-50 mg and wherein, the antidepressant is administered for 1-30 days before the psychedelic and reduces effects chosen from the group consisting of bad drug effects, anxiety, autonomic effects, adverse effects of the psychedelic, and combinations thereof.

2. The method of claim 1, wherein treatment with the antidepressant is maintained during administering the psychedelic.

3. The method of claim 2, further including a step chosen from the group consisting of avoiding a withdrawal syndrome from the antidepressant, avoiding relapse of depression, avoiding relapse of anxiety, avoiding relapse of a disorder for which the individual is treated with the antidepressant, and combinations thereof.

4. The method of claim 1, wherein the individual has a psychiatric disorder chosen from the group consisting of depression, anxiety, anxiety related to life-threatening disease, obsessive-compulsive disorder, personality disorder, and addiction.

5. The method of claim 1, wherein said step of administering an antidepressant reduces bad drug effects chosen from the group consisting of anxiety, fear, fear of loss of body control, anxious-ego dissolution, disembodiment, fear of impaired thought control, paranoia, panic, negative thoughts, grooming, nadir effects, increases in blood pressure, increases in body temperature, increases in pupil size, acute and subacute adverse effects, and combinations thereof.

6. The method of claim 1, wherein said step of administering an antidepressant does not interfere with the psychedelic improving good drug effects chosen from the group consisting of drug linking, oceanic boundlessness, experience of unity, spiritual experience, blissful state, insightfulness, connectedness, mystical experiences, mystical-type effects, positive mood, transcendence of time/space, ineffability, well-being, trust, feelings of love, feeling open, peak experience, and combinations thereof.

7. The method of claim 1, wherein the psychedelic is administered repeatedly and/or at a low dose.

8. The method of claim 1, wherein the individual has an increased risk for adverse events caused by psychedelic administration.

* * * * *